(12) United States Patent
Mrsny

(10) Patent No.: US 10,662,222 B2
(45) Date of Patent: May 26, 2020

(54) DRUG DELIVERY ENHANCEMENT AGENTS

(71) Applicant: The University of Bath, Bath (GB)

(72) Inventor: Randall Jay Mrsny, Bath (GB)

(73) Assignee: The University of Bath, Bath (GB)

( * ) Notice: Subject to any disclaimer, the term of this patent is extended or adjusted under 35 U.S.C. 154(b) by 315 days.

(21) Appl. No.: 15/314,424

(22) PCT Filed: Jun. 12, 2015

(86) PCT No.: PCT/GB2015/051741
§ 371 (c)(1),
(2) Date: Nov. 28, 2016

(87) PCT Pub. No.: WO2015/189641
PCT Pub. Date: Dec. 17, 2015

(65) Prior Publication Data
US 2017/0183379 A1    Jun. 29, 2017

(30) Foreign Application Priority Data
Jun. 12, 2014    (GB) ...................... 1410507

(51) Int. Cl.
*C07K 7/06* (2006.01)
*C07K 7/08* (2006.01)
(Continued)

(52) U.S. Cl.
CPC .............. *C07K 7/06* (2013.01); *A61K 9/0053* (2013.01); *A61K 38/07* (2013.01); *A61K 38/08* (2013.01); *A61K 38/10* (2013.01); *A61K 38/26* (2013.01); *A61K 38/28* (2013.01); *A61K 38/465* (2013.01); *C07K 5/10* (2013.01); *C07K 7/08* (2013.01); *C12N 9/16* (2013.01); *C12Y 301/03016* (2013.01); *C07K 2319/10* (2013.01)

(58) Field of Classification Search
CPC .... A61K 2300/00; A61K 38/26; A61K 38/28; A61K 38/07; A61K 38/08; A61K 38/10; A61K 38/465; A61K 9/0053; C07K 2319/10; C07K 5/10; C07K 7/06; C07K 7/08; C12N 9/16; C12Y 301/03016
See application file for complete search history.

(56) References Cited

U.S. PATENT DOCUMENTS 5,700,486 A    12/1997  Canal et al.
6,127,339 A  * 10/2000  Hatanaka ........... C07K 5/06156
                                                    514/21.6
(Continued)

FOREIGN PATENT DOCUMENTS

WO    WO 2008/137681    11/2008

OTHER PUBLICATIONS

Urwin et al., Heterogeneity of the PorB Protein in Serotype 22 Neisseria meningitidis, Journal of Clinical Microbiology, vol. 36:3680-3682 (Dec. 1998) (Year: 1998).*
(Continued)

*Primary Examiner* — Randall L Beane
(74) *Attorney, Agent, or Firm* — Carol L. Francis; Bozicevic, Field & Francis LLP

(57) ABSTRACT

A peptide comprising a sequence for opening a tight junction of an epithelial surface and optionally a cell penetrating sequence; and related compositions, optionally comprising further pharmaceutical agents; and related methods.

23 Claims, 11 Drawing Sheets
Specification includes a Sequence Listing.

(51) Int. Cl.

| | | |
|---|---|---|
| A61K 38/28 | (2006.01) | |
| A61K 38/26 | (2006.01) | |
| A61K 9/00 | (2006.01) | |
| A61K 38/08 | (2019.01) | |
| A61K 38/10 | (2006.01) | |
| A61K 38/46 | (2006.01) | |
| C12N 9/16 | (2006.01) | |
| A61K 38/07 | (2006.01) | |
| C07K 5/10 | (2006.01) | |

(56) References Cited

U.S. PATENT DOCUMENTS

| | | | |
|---|---|---|---|
| 6,447,743 | B1 | 9/2002 | Devic et al. |
| 7,553,944 | B2* | 6/2009 | Yuen .................... C07K 14/005 424/185.1 |
| 2003/0175285 | A1* | 9/2003 | Klinguer-Hamour ... C07K 7/08 424/185.1 |
| 2004/0031072 | A1 | 2/2004 | La Rosa et al. |
| 2004/0214272 | A1* | 10/2004 | La Rosa ................ C07H 21/04 435/69.1 |
| 2008/0207502 | A1* | 8/2008 | Rastelli .................... C07K 7/06 514/8.1 |
| 2010/0234283 | A1* | 9/2010 | Kaumaya ................ C07K 14/52 514/8.1 |
| 2011/0236397 | A1* | 9/2011 | Reiser ................. A61K 38/4873 424/158.1 |
| 2011/0293557 | A1* | 12/2011 | Prieto Valtuena .......................... A61K 38/1709 424/85.2 |
| 2012/0077749 | A1* | 3/2012 | Scheiflinger ............. C07K 7/06 514/13.7 |
| 2013/0216564 | A1* | 8/2013 | Pravin .................... C07K 14/52 424/185.1 |
| 2013/0345135 | A1* | 12/2013 | Moss ................. C07K 14/4716 514/12.4 |
| 2014/0296479 | A1* | 10/2014 | Jon .................... G01N 33/5308 530/324 |

OTHER PUBLICATIONS

Akram et al., Amino acids: A review article, J. Med. Plant. Res., vol. 5(17):3997-4000 (Sep. 2011) (Year: 2011).*
Fletcher et al., Partially Modified Retro-Inverso Peptides: Development, Synthesis, and Conformational Behavior, Chem. Rev., vol. 98:763-795 (1998) (Year: 1998).*
Fischer, The Design, Synthesis and Application of Stereochemical and Directional Peptide Isomers: A Critical Review, Current Protein and Peptide Science, vol. 4:339-356 (2003) (Year: 2003).*
Chorev, A Dozen Years of Retro-Inverso Peptidomimetics, Acc. Chem. Res., vol. 26:266-273 (1993) (Year: 1993).*
Livingstone et al., Protein sequence alignments: a strategy for the hierarchical analysis of residue conservation, CABIOS, vol. 9(6): 745-756 (1993) (Year: 1993).*
A J Sabat, et al. (2013) "Novel organization of the arginine catabolic mobile element and staphylococcal cassette chromosome mec composite island and its horizontal transfer between distinct *Staphylococcus aureus* genotypes", Antimicrobial Agents and Chemotherapy, 57(11):5774-5777.
R J Mrsny et al, (2008) "A key claudin extracellular loop domain is critical for epithelial barrier integrity", American Journal of Pathology., 172(4):905-915.
K Kilk et al., (2009) "Analysis of in vitro toxicity of five cell-penetrating peptides by metabolic profiling", Toxicology., 265(1):87-95.
A Taverner et al., (2015) "Enhanced paracellular transport of insulin can be achieved via transient induction of myosin light chain phosphorylation", Journal of Controlled Release., 210:189-197.
Anderberg, E.K., et al., (1993) "Sodium caprate elicits dilatations in human intestinal tight junctions and enhances drug absorption by the paracellular route", Pharmaceutical Research, 10(6):857-864.

Balda, M.S., et al., (1996) "Functional dissociation of paracellular permeability and transepithelial electrical resistance and disruption of the apical-basolateral intramembrane diffusion barrier by expression of a mutant tight junction membrane protein", J Cell Biol, 134:1031-1049.
Blume, L.F., et al., (2010) "Temperature corrected transepithelial electrical resistance (TEER) measurement to quantify rapid changes in paracellular permeability", Pharmazie, 65:19-24.
Brayden, D., et al. (1997) "Heparin absorption across the intestine: effects of sodium N-[8-(2-hydroxybenzoyl)amino]caprylate in rat in situ intestinal instillations and in Caco-2 monolayers", Pharm Res, 14(12):1772-1779.
Brayden, D.J., and Maher, S., (2010) "Oral absorption enhancement: taking the next steps in therapeutic delivery", Therapeutic Delivery, 1(1):5-9.
Campos, A. & Vasconcelos, V., (2010) "Molecular mechanisms of microcystin toxicity in animal cells", International Journal of Molecular Sciences, 11:268-287.
Carino, G.P. & Mathiowitz, E., (1999) "Oral insulin delivery", Advanced Drug Delivery Reviews, 35:249-257.
Castelli, M.C., et al., (2011) "Pharmacokinetics of oral cyanocobalamin formulated with sodium N-[8-(2-hydroxybenzoyl)amino]caprylate (SNAC): an open-label, randomized, single-dose, parallel-group study in healthy male subjects", Clin Ther, 33:934-945.
Chatterjee, J. et al., (2012) "Development of a peptide that selectively activates protein phosphatase-1 in living cells", Angewandte Chemie 51, 10054-10059.
Cho, S.Y. et al., (2002) "Enhancement of paracellular transport of heparin disaccharide across Caco-2 cell monolayers", Archives of Pharmacal Research, 25(1):86-92.
Cunningham, K.E. & Turner, J.R., (2012) "Myosin light chain kinase: pulling the strings of epithelial tight junction function", Annals of the New York Academy of Sciences, 1258(1):34-42.
Del Vecchio, G., et al., (2012) "Sodium caprate transiently opens claudin-5-containing barriers at tight junctions of epithelial and endothelial cells", Mol. Pharm., 9:2523-2533.
Deli, M.A., (2009) "Potential use of tight junction modulators to reversibly open membranous barriers and improve drug delivery", Biochimica et Biophysica Acta 1788, pp. 892-910.
Duizer, E., et al., (1998) "Absorption enhancement, structural changes in tight junctions and cytotoxicity caused by palmitoyl carnitine in Caco-2 and IEC-18 cells", The Journal of Pharmacology and Experimental Therapeutics, 287(1):395-402.
Dunican, D.J. & Doherty, P., (2001) "Designing cell-permeant phosphopeptides to modulate intracellular signaling pathways", Biopolymers, 60:45-60.
Eto, M., (2009) "Regulation of cellular protein phosphatase-1 (PP1) by phosphorylation of the CPI-17 family, C-kinase-activated PP1 inhibitors", J Biol Chem, 284(51):35273-35277.
Fischer, P.M., (2003) "The design, synthesis and application of stereochemical and directional peptide isomers: a critical review", Curr Protein Pept Sci, 4:339-356.
Goldberg, J., et al., (1995) "Three-dimensional structure of the catalytic subunit of protein serine/threonine phosphatase-1", Nature, 376:745-753.
Gonzalez-Mariscal, L., et al., (2008) "Crosstalk of tight junction components with signaling pathways", Biochim Biophys Acta 1778, pp. 729-756.
Grassie, M.E., et al., (2011) "The myosin phosphatase targeting protein (MYPT) family: a regulated mechanism for achieving substrate specificity of the catalytic subunit of protein phosphatase type 1delta", Archives of Biochemistry and Biophysics, 510:147-159.
Grunwald, J., et al., (2009) "TAT Peptide and Its Conjugates: Proteolytic Stability", Bioconjug Chem, 20(8):1531-1537.
Harrison, G.A., (1923) "Insulin in Alcoholic Solution by the Mouth", British Medical Journal, 2:1204-1205.
Hayashi, Y., et al., (2001) "Defining the structural determinants and a potential mechanism for inhibition of myosin phosphatase by the protein kinase C-potentiated inhibitor protein of 17 kDa", J Biol Chem, 276(43):39858-39863.

(56) References Cited

OTHER PUBLICATIONS

Hirano, K., (2007) "Current topics in the regulatory mechanism underlying the Ca2+ sensitization of the contractile apparatus in vascular smooth muscle", Journal of Pharmacological Sciences, 104:109-115.
Jones, S.W. et al., (2005) "Characterisation of cell-penetrating peptide-mediated peptide delivery", Br J Pharmacol, 145:1093-1102.
Karsdal, M.A., et al., (2011) "Lessons learned from the development of oral calcitonin: the first tablet formulation of a protein in phase III clinical trials", J Clin Pharmacol, 51:460-471.
Lindmark, T., et al., (1998) "Absorption enhancement in intestinal epithelial Caco-2 monolayers by sodium caprate: assessment of molecular weight dependence and demonstration of transport routes", J Drug Target, 5(3):215-223.
Lindmark, T., et al., (1997) "Mechanism of absorption enhancement in humans after rectal administration of ampicillin in suppositories containing sodium caprate", Pharm Res, 14(7):930-935.
Liu, F., et al., (2009) "Preparation of orthogonally protected (2S, 3R)-2-amino-3-methyl-4-phosphonobutyric acid (Pmab) as a phosphatase-stable phosphothreonine mimetic and its use in the synthesis of polo-box domain-binding peptides", Tetrahedron, 65:9673-9679.
MacKintosh, C., et al., (1990) "Cyanobacterial microcystin-LR is a potent and specific inhibitor of protein phosphatases 1 and 2A from both mammals and higher plants", FEBS letters, 264(2):187-192.
Madani, F., et al., (2011) "Mechanisms of cellular uptake of cell-penetrating peptides", Journal of Biophysics, 2011(414729):1-10.
Maher, S., et al., (2009) "Safety and efficacy of sodium caprate in promoting oral drug absorption: from in vitro to the clinic", Adv Drug Deliv Rev, 61:1427-1449.
Matsumura, F., and Hartshorne, D.J., (2008) "Myosin phosphatase target subunit: Many roles in cell function", Biochem Biophys Res Commun, 369:149-156.
Matter, K. & Balda, M.S., (2003) "Functional analysis of tight junctions", Methods, 30:228-234.
Milletti, F., (2012) "Cell-penetrating peptides: classes, origin, and current landscape", Drug Discovery Today, 17(15/16):850-860.
Milstein, S.J., et al., (1998) "Partially unfolded proteins efficiently penetrate cell membranes—implications for oral drug delivery", J Control Release, 53:259-267.
Mirzapoiazova, T., et al., (2011) "Non-muscle myosin light chain kinase isoform is a viable molecular target in acute inflammatory lung injury", Am J Respir Cell Mol Biol, 44:40-52.
Mosmann, T., (1983) "Rapid colorimetric assay for cellular growth and survival: application to proliferation and cytotoxicity assays", J Immunol Methods, 65:55-63.
Murthy, K.S., et al., (2003) "Differential signalling by muscarinic receptors in smooth muscle: m2-mediated inactivation of myosin light chain kinase via Gi3, Cdc42/Rac1 and p21-activated kinase 1 pathway, and m3-mediated MLC20 (20 kDa regulatory light chain of myosin II) phosphorylation via Rho-associated kinase/myosin phosphatase targeting subunit 1 and protein kinase C/CPI-17 pathway", Biochem J, 374:145-155.
Owens, S.E., et al., (2005) "A strategy to identify stable membrane-permeant peptide inhibitors of myosin light chain kinase", Pharm Res, 22(5):703-709.
Pappenheimer, J.R., (1993) "On the coupling of membrane digestion with intestinal absorption of sugars and amino acids", The American Journal of Physiology, 265:G409-417.
Petersen, S.B. et al., (2012) "Evaluation of alkylmaltosides as intestinal permeation enhancers: comparison between rat intestinal mucosal sheets and Caco-2 monolayers", European Journal of Pharmaceutical Sciences, 47:701-712.
Peterson, M.D., and Mooseker, M.S., (1992) "Characterization of the enterocyte-like brush border cytoskeleton of the C2BBe clones of the human intestinal cell line, Caco-2", J Cell Sci, 102:581-600.
Peti, W., et al., (2012) "Structural basis for protein phosphatase 1 regulation and specificity", The FEBS Journal, 280:1-16.

Pilkis, S.J. & Granner, D.K., (1992) "Molecular physiology of the regulation of hepatic gluconeogenesis and glycolysis", Annual Review of Physiology, 54: gb885-909.
Rapoport, M., and Lorberboum-Galski, H., (2009) "TAT-based drug delivery system—new directions in protein delivery for new hopes?", Expert Opin Drug Deliv, 6:453-463.
Rodgers, L.S., and Fanning, A.S., (2011) "Regulation of epithelial permeability by the actin cytoskeleton", Cytoskeleton (Hoboken), 68:653-660.
Rubas, W., et al., (1996) "An integrated method to determine epithelial transport and bioactivity of oral drug candidates in vitro", Pharmaceutical Research, 13:23-26.
Rubas, W., et al., (1996) "Flux measurements across Caco-2 monolayers may predict transport in human large intestinal tissue", J Pharm Sci, 85:165-169.
Sillerud, L.O. & Larson, R.S., (2005) "Design and structure of peptide and peptidomimetic antagonists of protein-protein interaction", Curr Protein Pept Sci, 6:151-169.
Terrak, M., et al., (2004) "Structural basis of protein phosphatase 1 regulation", Nature, 429(17):780-784.
Turner, J.R., (2009) "Intestinal mucosal barrier function in health and disease", Nat Rev Immunol, 9:799-809.
Turner, J.R., (2006) "Molecular basis of epithelial barrier regulation: from basic mechanisms to clinical application", The American Journal of Pathology, 169:1901-1909.
Turner, J.R. et al., (1997) "Physiological regulation of epithelial tight junctions is associated with myosin light-chain phosphorylation", The American Journal of Physiology, 273:C1378-1385.
Wender, P.A., et al., (2005) "Dendrimeric molecular transporters: synthesis and evaluation of tunable polyguanidino dendrimers that facilitate cellular uptake", Org Letters, 7(22):4815-4818.
Woodsome, T.P., et al., (2006) "Agonist- and depolarization-induced signals for myosin light chain phosphorylation and force generation of cultured vascular smooth muscle cells", J Cell Sci, 119(9):1769-1780.
Xiao, C., et al., (2011) "Defective epithelial barrier function in asthma", J Allergy Clin Immunol, 128:549-556.
Zolotarevsky, Y., et al., (2002) "A membrane-permeant peptide that inhibits MLC kinase restores barrier function in in vitro models of intestinal disease", Gastroenterology, 123:163-172.
Clayburgh, et al., (2005) "Epithelial myosin light chain kinase—dependent barrier dysfunction mediates T cell activation—induced diarrhea in vivo", J. Clin. Invest., 115:2702-2715.
Ohki S, et al., (2003) "Distinctive Solution Conformation of Phosphatase Inhibitor CPI-17 Substituted with Aspartate at the Phosphorylation-site Threonine Residue", Journal of Molecular Biology, 326(5)1539-1547.
Nishimura J, et al., (2003) Nihon yakurigaku zasshi. Folia pharmacologica Japonica, Japan, vol. 122 Suppl., (MEDLINE abstract).
Srinivas S, et al., (2006) "Histamine-Induced Phosphorylation of the Regulatory Light Chain of Myosin II Disrupts the Barrier Integrity of Corneal Endothelial Cells", IOVS, Voo., 47(9):4011-4018.
Carter, E., et al., (Mar. 2013) "Cell Penetrating Peptides Fail to Induce an Innate Immune Response in Epithelial Cells In Vitro: Implications for Continued Therapeutic Use", European Journal of Pharmaceutics and Biopharmaceutics, 85:12-19.
Grover, M. & Utreja, P., (Jun. 2014) "Recent Advances in Drug Delivery Systems for Anti-Diabetic Drugs: A Review", Current Drug Delivery, 11:444-457.
Krug, S.M. et al., (Jul. 2012) "Sodium Caprate as an Enhancer of Macromolecule Permeation Across Tricellular Tight Junctions of Intestinal Cells" Biomaterials, 34:275-282.
Petersen, S.B. et al., (Jan. 2013) Colonic Absorption of Salmon Calcitonin Using Tetradecyl Maltoside (TDM) as a Permeation Enhancer, European Journal of Pharmaceutical Sciences, 48:726-734.
Vasconcelos, L., et al., (May 2013) "Therapeutic Potential of Cell-Penetrating Peptides", Therapeutic Delivery, 4(5):573-591.
Welling, S.H. et al., (Aug. 2013) "The Role of Citric Acid in Oral Peptide and Protein Formulations: Relationship between Calcium Chelation and Proteolysis Inhibition", European Journal of Pharmaceutics and Biopharmaceutics, 8 pages.

(56) References Cited

OTHER PUBLICATIONS

Yun, Y., et al., (Oct. 2012) "Nanoparticles for Oral Delivery: Targeted Nanoparticles with Peptidic Ligands for Oral Protein Delivery", Advanced Drug Delivery Reviews, 65:822-832.

Almansour, Khaled, et al., (Mar. 2018) "Mechanistic studies of a cell-permeant peptide designed to enhance myosin light chain phosphorylation in polarized intestinal epithelia", Journal of Controlled Release, 279:208-219.

Urwin, Rachel, et al., (1998) "Heterogeneity of the PorB Protein in Serotype 22 Neisseria meningitidis", Journal of Clinical Microbiology, 36(12):3680-3682.

\* cited by examiner

DRUG DELIVERY ENHANCEMENT AGENTS

BACKGROUND TO INVENTION

Epithelial cells constitute a barrier to drug delivery. For example, the absorption of orally-administered therapeutics may be limited by the gut epithelium, and the absorption of therapeutics delivered by inhalation may be limited by the lung epithelium. Likewise, the absorption of therapeutics delivered to other epithelial sites, such as the rectal cavity, buccal cavity, vaginal cavity, nasal cavity or by topical administration to the skin may be similarly limited by an epithelial barrier. This barrier presents a challenge to the delivery of a wide range of drugs including small molecules, peptides, proteins, vaccines and nucleic acids. Various attempts have been made to mitigate the effect of the barrier to drug absorption provided by epithelia. However, many of those attempts involve the use of agents which either deliberately or as an unintended side effect damage the epithelium. Such damage may result in uncontrolled passage of materials across the epithelium, and that, in possible combination with immunological danger signals resulting from cellular damage, may result in unwanted inflammation of the epithelium. There therefore exists a need for improved technique of assisting the passage of therapeutic agents across an epithelial surface, preferably in a manner which is controlled, temporarily and results in no unacceptable cellular damage (Brayden & Maher (2000) Therapeutic Delivery 1 (1):5-9).

The challenge to drug absorption presented by the epithelium has resulted in some drugs needing to be delivered by routes other than across an epithelium, for example by sub-cutaneous injection. This brings a number of disadvantages including reduced patient acceptability, lower patient compliance and higher costs associated with using and storing liquid formulations, providing injection devices and disposing of used injection devices in a safe and responsible way.

The epithelium provides a barrier to the absorption of drugs because it comprises a layer of cells which are connected to each other by tight junctions which provide a seal against many substances but which can be transiently opened. There exists a need to be able to better control tight junction opening to assist in the delivery of therapeutics. A number of solutions to the problem of opening tight junctions have been proposed. These efforts have led to the identification of two sets of molecules: non-native, extended amino acids (NEAAs) and short-chain fatty acids (SCFAs). NEAAs have been developed primarily by the company Emisphere who have demonstrated marginal improvements in drug uptake but have yet to submit an application for the regulatory approval of a new drug. One SCFA, sodium caprate is used in an approved rectal suppository product to improve the uptake of ampicillin. It is suspected however that the mechanism of improved uptake is through local damage of the mucosal epithelium (Maher et al. (2009) Adv. Drug Deliv. Rev. 61:1427-1449).

There is particular interest in the oral delivery of insulin, glucagon like peptide 1 (GLP-1) and other related molecules for the treatment of diabetics, obesity, suppression of appetite and improvement of carbohydrate metabolism. Such compounds are especially in need of an oral delivery route because they are typically administered for months, years or more, meaning that avoiding injections would significantly increase patient acceptability and potentially lower cost, and also because in nature these gut hormones enter the blood stream of the subject via the hepatic portal vein and delivery across an intestinal barrier would more closely mimic the physiological delivery route.

The present invention is based on the discovery of compounds useful for the controlled opening of epithelial tight junctions.

SUMMARY OF INVENTION

According to a first aspect of the invention there is provided a peptide comprising a sequence according to Formula 1:

$$\text{Formula 1} \quad (\text{SEQ ID NO: 1})$$
$$X_4\text{-}X_5\text{-}X_6\text{-}X_7\text{-}X_8$$

Wherein:

$X_4$ is a negatively charged amino acid residue, for example pTyr, Asp or Glu;

$X_5$ is a small hydrophobic amino acid residue, for example Val or Ala;

$X_6$ is a positively charged amino acid residue, for example Lys or Arg;

$X_7$ is a hydrophilic amino acid residue, for example, Tyr, Phe, Thr or Ser; and $X_8$ is a negatively charged amino acid residue, for example pTyr, Asp or Glu, or comprising a sequence according to Formula 2

$$\text{Formula 2} \quad (\text{SEQ ID NO: 2})$$
$$X_5\text{-}X_6\text{-}X_7\text{-}X_8$$

wherein:

$X_5$ is any amino acid residue;

$X_6$ is Tyr;

$X_7$ is Gln; and $X_8$ is Tyr, or comprising a retro-inverso form of the sequence according to Formula 1 or Formula 2 wherein all amino acid residues are in the D-configuration and the peptide sequence order is reversed.

According to a second aspect of the invention there is provided a pharmaceutical composition comprising a peptide comprising sequence according to Formula 1

$$\text{Formula 1} \quad (\text{SEQ ID NO: 1})$$
$$X_4\text{-}X_5\text{-}X_6\text{-}X_7\text{-}X_8$$

wherein:

$X_4$ is a negatively charged amino acid residue, for example pTyr, Asp or Glu;

$X_5$ is a small hydrophobic amino acid residue, for example Val or Ala;

$X_6$ is a positively charged amino acid residue, for example Lys or Arg;

$X_7$ is a hydrophilic amino acid residue, for example, Tyr, Phe, Thr or Ser; and $X_8$ is a negatively charged amino acid residue, for example pTyr, Asp or Glu, and/or a peptide comprising a sequence according to Formula 2

Formula 2 (SEQ ID NO: 2)

$X_5-X_6-X_7-X_8$ wherein:

$X_5$ is any amino acid residue;
$X_6$ is Tyr;
$X_7$ is Gln; and
$X_8$ is Tyr;

or wherein the sequence according to Formula 1 and/or Formula 2 is in retro-inverso configuration wherein all amino acid residues are in the D-configuration and the peptide sequence order is reversed, and a pharmaceutically acceptable carrier.

According to a third aspect of the invention there is provided a peptide according to the first aspect of the invention or a pharmaceutical composition according to the second aspect of the invention for use as a medicament.

According to a fourth aspect of the invention there is provided use of a peptide according to the first aspect of the invention or a pharmaceutical composition according to the second aspect of the invention for the manufacture of a medicament.

According to a fifth aspect of the invention there is provided a method of opening the tight junctions of an epithelial surface comprising administering an effective amount of a peptide according to the first aspect of the invention or a pharmaceutical composition according to the second aspect of the invention to the epithelium.

According to a sixth aspect of the invention there is provided a method of delivering an agent across an epithelial surface comprising administering said agent in conjunction with a peptide according to a first aspect of the invention or as part of pharmaceutical composition according to a second aspect of the invention.

DEFINITIONS

Figure 1:
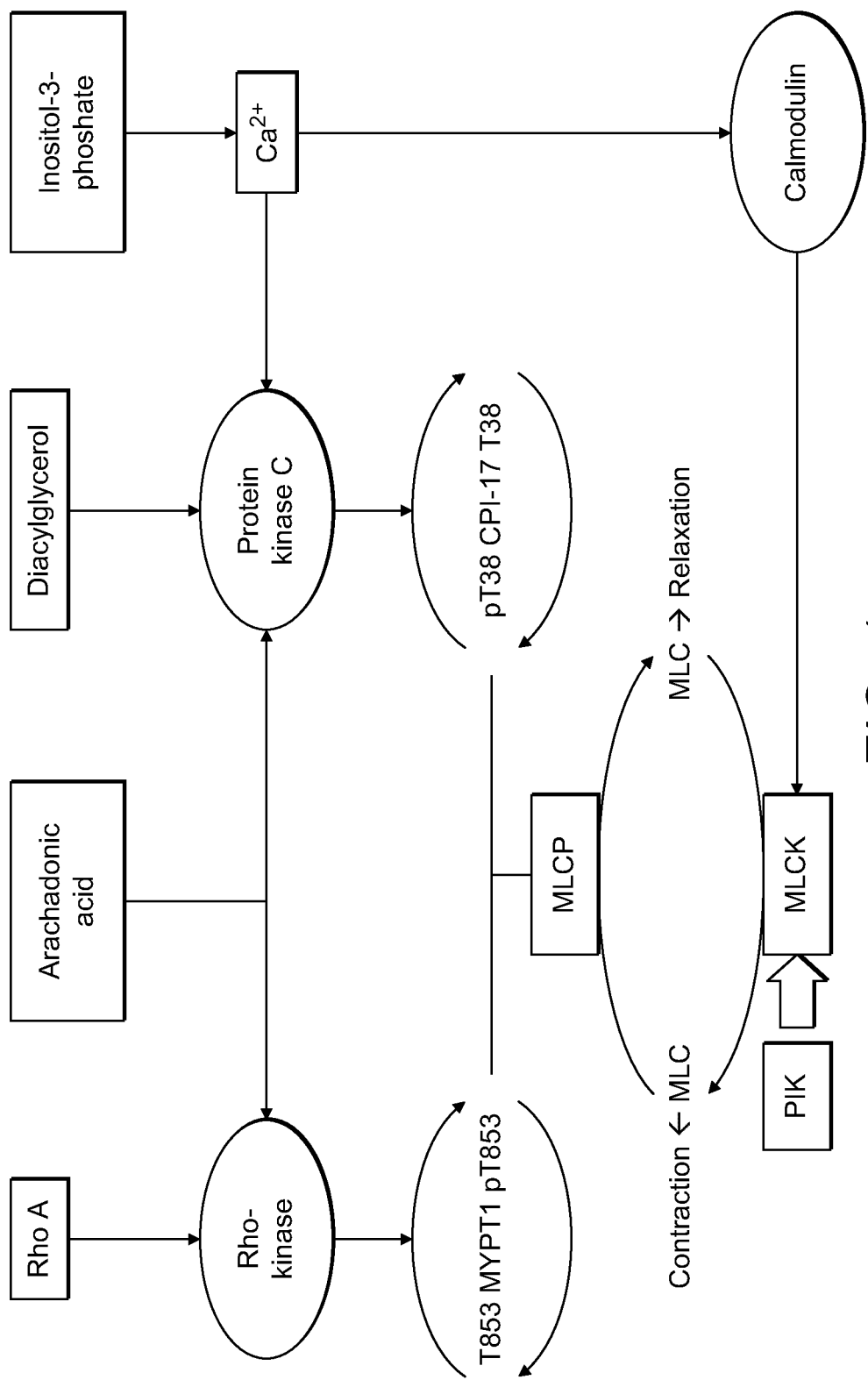
FIG. 1: Organisation of phosphatases and kinases known to regulate myosin light chain (MLC) phosphorylation status. Myosin light chain kinase (MLCK), which can phosphorylate MLC, is activated by an increase in cytoplasmic calcium ($Ca^{2+}$)-calmodulin levels. The activated form of MLCK can be inhibited by a small, membrane-permeable peptide inhibitor of kinase (PIK). The activity of myosin light chain phosphatase (MLCP) complex is controlled by two regulatory subunits known as CPI-17 and MYPT1. The actions of these regulatory subunits are, in turn, controlled by protein kinase C and Rho kinase activities, respectively.
Figure 2:
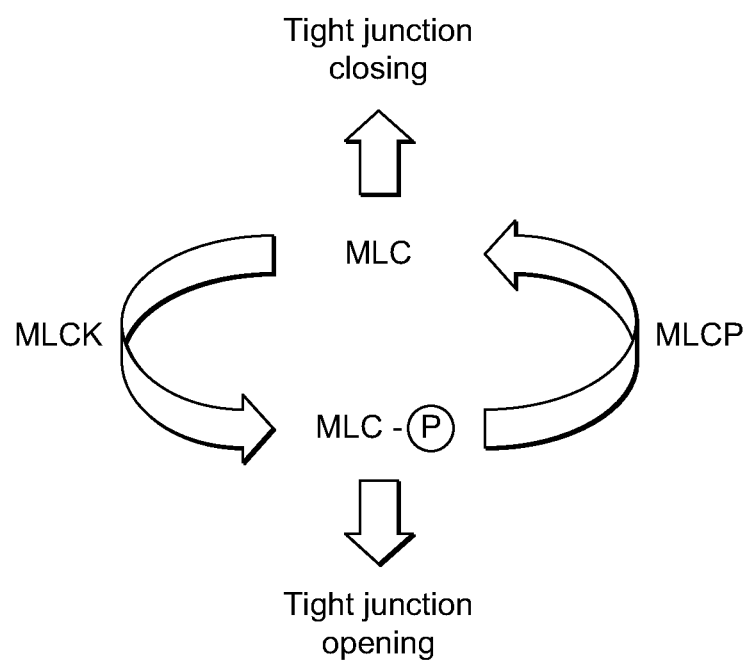
FIG. 2: Dynamic regulation of tight junction (TJ) opening/closing and MLC phosphorylation/dephosporylation. In the native state, MLCP is active; this maintains MLC in a de-phosphorylated state and TJ structures in a closed state where there is minimal paracellular (between adjacent epithelial cells) flux of solutes. Sustained activation of MLCK or suppression of MLCP would lead to an increased MLC phosphorylation state and an increase in paracellular solute flux.

Polypeptide: A polymer in which the monomers are amino acid residues which are joined together through amide bonds. When the amino acids are alpha-amino acids, either the L-optical isomer or the D-optical isomer can be used. The present invention relates to both L-isomers and D-isomers. Preferably the invention relates to D-isomers, in particular, but not exclusively, when the peptide comprises the reverse sequence to that specified in Formula 1 or 2. Such peptides are referred to as being in the "retro-inverso" form. The terms "polypeptide" or "protein" as used herein encompass any amino acid sequence and include modified sequences such as glycoproteins and sequences using naturally occurring and non-naturally occurring amino acids. The term "polypeptide" covers naturally occurring proteins, as well as those which are recombinantly or synthetically produced, and salts, solvates and derivatives of polypeptides. Peptides of the present invention are preferably amidated at their C-terminus.

Salts and solvates of peptides of the invention are preferably those wherein the counterion or associated solvent is pharmaceutically acceptable. However, salts and solvates having non-pharmaceutically acceptable counterions or associated solvents are within the scope of the present invention, for example, for use as intermediates.

Peptide Activity

Peptides relating to all aspects of the invention are preferably active in their ability to enhance paracellular transport. This may be measured in accordance with one of the methods detailed herein (especially in the Examples).

Salts and Solvates

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

Peptide Synthesis

Peptides of the invention may be made by any suitable technique for making peptides, including but not limited to conventional methodology, for example, synthesis from individual amino acids, especially step-wise synthesis using an automatic peptide synthesizer; modification of native peptides; or recombinant manufacturing techniques.

While it is possible for the peptides of the invention to be administered alone, it is preferable for it to be present in a pharmaceutical composition. Accordingly, the invention provides a pharmaceutical composition comprising a peptide of the invention, and a pharmaceutically acceptable carrier. Pharmaceutical compositions of the invention may take the form of a pharmaceutical formulation as described below.

Pharmaceutical Formulations

The pharmaceutical formulations relating to the invention include those suitable for oral, parenteral inhalation (including fine particle dusts or mists which may be generated by means of various types of metered doses, pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with a pharmaceutical carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds. The compounds can be formulated, for administration orally, with delivery agents or carriers that facilitate the transport of therapeutic macromolecules and highly charged compounds across cell membranes, especially in the small intestine. Such delivery agents or carriers may in addition inhibit enzymatic degradation of peptides during passage through the gastrointestinal (GI) tract and/or the formulation may include additional agents that protect against such degradation. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The peptide of the invention can also be delivered through the oral cavity by sublingual and/or buccal administration. Moulded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Excipients that can be included are, for instance, proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The peptides of the invention are also suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the peptides of the invention. These compositions exhibit certain biocompatibility features which allow a controlled release of the active substance. See U.S. Pat. No. 5,700,486.

A therapeutically effective amount of a peptide or pharmaceutical composition of the invention may be administered as a single pulse dose, as a bolus dose, or as pulse doses administered over time. Thus, in pulse doses, a bolus administration of a peptide or composition of the invention is provided, followed by the elapse of time period followed by a second bolus administration. In specific, non-limiting examples, pulse doses of a compound of the invention are administered during the course of a day, during the course of a week, or during the course of a month.

DETAILED DESCRIPTION OF THE INVENTION

The present invention is based on the development of strategies to open the paracellular route between adjacent cells in an epithelium by controlling the dynamic opening and closing of tight junctions by harnessing an endogenous control mechanism. The strategies related to the provision of peptide compounds designed de novo to target specific cellular targets and to have specific action on those targets.

Recent studies have suggested that chronic inflammation events that occur at simple mucosal surfaces, such as those of the intestine and airway, are associated with increase permeability of the epithelial barriers at these locations (4, 13). The basis for this increased permeability was determined to be an increased phosphorylation status of the tight junction (TJ)-associated cytosolic protein known as myosin light chain (MLC). This mechanism was verified by the identification and in vivo testing of a nine amino acid, membrane-permeable peptide that selectively inhibited MLC phosphorylation. The knowledge of endogenous mechanism of intestinal cell regulation of MLC phosphorylation, was used to design two classes of peptides to selectively alter the actions of myosin phosphatase target subunit 1 (MYPT1) or 17 KDa L-kinase potentiated protein phosphatase-1 inhibitor (CPI-17) proteins. These two proteins function to reduce MLC phosphorylation and the present invention relates to transient inhibition of their function so as to transiently increase paracellular permeability of an epithelium. The two target proteins regulate MLC phosphorylation at different rates and by providing agents and methods selectively targeting those two different proteins, it is possible to finally control the time course of opening and reclosing of the tight junctions.

According to a first aspect of the invention there is provided a peptide comprising sequence According to Formula 1:

Formula 1
(SEQ ID NO: 1)
$X_4-X_5-X_6-X_7-X_8$ wherein:

$X_4$ is a negatively charged amino acid residue, for example pTyr, Asp or Glu;

$X_5$ is a small hydrophobic amino acid residue, for example Val or Ala;

$X_6$ is a positively charged amino acid residue, for example Lys or Arg;

$X_7$ is a hydrophilic amino acid residue, for example, Tyr, Phe, Thr or Ser; and $X_8$ is a negatively charged amino acid residue, for example pTyr, Asp or Glu.

or comprising sequence according to Formula 2

Formula 2
(SEQ ID NO: 2)
$X_5-X_6-X_7-X_8$ wherein:

$X_5$ is any amino acid residue;

$X_6$ is Tyr;

$X_7$ is Gln; and $X_8$ is Tyr;

or comprising a retro-inverso form of the sequence according to Formula 1 or Formula 2 wherein all amino acid residues are in the D-configuration and the peptide sequence order is reversed.

Formula 1 defines a sequence which targets PP1-CP1-17 interactions. Formula 2 defines a sequence which targets PP1-MYPT1 interactions. The unifying feature of both sequences is that they both act to reduce MLC phosphorylation and therefore their inhibition leads to an increased phosphorylation of MLC and opening of the tight junctions of an epithelium.

According to some embodiments of all aspects of the invention the functional feature of reducing MLC phosphorylation may be a feature of the claimed invention.

Sequences of Formula 1

Peptides according to formula 1 inhibit PP1-CP1-17 interactions. According to some embodiments of the various aspects of the invention according to the sequence encompassed by Formula 1 wherein $X_4$ is pTyr, Asp or Glu;
$X_5$ is Val or Ala;
$X_6$ is Lys or Arg;
$X_7$ is Tyr, Phe, Thr or Ser; and
$X_8$ is pTyr, Asp or Glu.

According to some embodiments:
$X_4$ is Asp or Glu;
$X_5$ is Val or Ala;
$X_6$ is Lys or Arg;
$X_7$ is Tyr, Phe or Thr; and
$X_8$ is Asp or Glu.

According to some embodiments:
$X_4$ is Asp or Glu;
$X_5$ is Val;
$X_6$ is Lys;
$X_7$ is Tyr; and
$X_8$ is Asp or Glu.

According to some embodiments:
$X_4$ is Glu;
$X_5$ is Val;
$X_6$ is Lys;
$X_7$ is Tyr; and
$X_8$ is Asp.

The sequences according to various embodiments of Formula 1, define the PP1-CP1-17 targeting motif. In order to function effectively in some embodiments of the invention, a peptide comprising a sequence according to Formula 1, also contains sequence to ensure its delivery into the cytosol of epithelial cells where it has its target. Such a sequence may be a cell penetration-promoting sequence or a sequence that promotes cell surface binding to epithelial cells followed by phagocytosis into that cell. According to certain preferred embodiments a sequence according to Formula 1 is (Formula 1a)
(SEQ ID NO: 5)
$X_1-X_2-X_3-X_4-X_5-X_6-X_7-X_8-X_9-X_{10}$,
or (SEQ ID NO: 6)
$X_3-X_4-X_5-X_6-X_7-X_8-X_9-X_{10}$,
or (SEQ ID NO: 7)
$X_1-X_2-X_3-X_4-X_5-X_6-X_7-X_8$, most preferably (SEQ ID NO: 5)
$X_1-X_2-X_3-X_4-X_5-X_6-X_7-X_8-X_9-X_{10}$ wherein:

$X_1$ is up to 10 positively charged amino acid residues;
$X_2$ is a positively charged amino acid residue;
$X_3$ is absent or a hydrophobic amino acid residue;
$X_4$ is a negatively charged amino acid residue;
$X_5$ is a small hydrophobic amino acid residue;
$X_6$ is a positively charged amino acid residue;
$X_7$ is a hydrophobic amino acid residue;

$X_8$ is a negatively charged amino acid residue;
$X_9$ is a positively charge amino acid residue; and
$X_{10}$ is up to 10 positively charged amino acid residues; or wherein all amino acid residues are in the D-configuration and the peptide sequence order is reversed.

According to certain embodiments of the alternative formulae given immediately above, as relating to all aspects of the present invention,
$X_1$ is up to 10 positively charge amino acid residues;
$X_2$ is a positively charged amino acid residue;
$X_3$ is Val, Ala, Leu or Ile;
$X_4$ is pTyr, Asp or Glu;
$X_5$ is Val or Arg;
$X_6$ is Lys or Arg;
$X_7$ is Tyr, Phe, Thr or Ser;
$X_8$ is pTyr, Asp or Glu;
$X_9$ is a positively charged amino acid residue; and
$X_{10}$ is up to 10 positively charged amino acid residues; or all amino acid residues are in the D-configuration and the peptide sequence order is reversed.

According to some embodiments:
$X_1$ is up to 10 residues of Lys or Arg;
$X_2$ is Lys or Arg;
$X_3$ is Ala or Val;
$X_4$ is pTyr, Asp or Glu;
$X_5$ is Val or Arg;
$X_6$ is Lys or Arg;
$X_7$ is Tyr, Phe Thr or Ser;
$X_8$ is pTyr, Asp or Glu;
$X_9$ is Lys or Arg; and
$X_{10}$ is up to 10 residues of Lys or Arg.

According to some embodiments:
$X_1$ is Lys or Arg;
$X_2$ is Lys or Arg;
$X_3$ is Ala or Val;
$X_4$ is Asp or Glu;
$X_5$ is Val;
$X_6$ is Lys;
$X_7$ is Tyr;
$X_8$ is Asp or Glu;
$X_9$ is Lys or Arg; and
$X_{10}$ is Lys or Arg.

According to some embodiments:
$X_1$ is Lys or Arg;
$X_2$ is Lys or Arg;
$X_3$ is Val;
$X_4$ is Glu;
$X_5$ is Val;
$X_6$ is Lys;
$X_7$ is Tyr;
$X_8$ is Asp;
$X_9$ is Lys or Arg; and
$X_{10}$ is Lys or Arg.

According to some embodiments:

$X_1$-$X_2$-$X_3$-$X_4$-$X_5$-$X_6$-$X_7$-$X_8$-$X_9$-$X_{10}$
(SEQ ID NO: 3)
Is $Arg_1$-$Arg_2$-$Val_3$-$Glu_4$-$Val_5$-$Lys_6$-$Tyr_7$-$Asp_8$-$Arg_9$-$Arg_{10}$.

The invention also comprises, in certain embodiments, the retro-inverso form of the sequences given above.

Sequences of Formula 2

Peptides according to Formula 2 inhibit PP1-MYPT1 interactions. According to some embodiments of the various aspects of the invention according to the sequence encompassed by Formula 2 wherein:

$X_5$ is a positively charged amino acid residue;
$X_6$ is Tyr;
$X_7$ is Gln, and
$X_8$ is Tyr.

According to some embodiments:
$X_5$ is Lys or Arg;
$X_6$ is Tyr;
$X_7$ is Gln; and
$X_8$ is Tyr.

According to some embodiments:
$X_5$ is Lys;
$X_6$ is Tyr;
$X_7$ is Gln; and
$X_8$ is Tyr.

The invention also comprises, in certain embodiments, the retro-inverso form of the sequences given above.

The sequences according to various embodiments of Formula 2, define the PP1-MYPT1 targeting motif. In order to function effectively in some embodiments of the invention, a peptide comprising a sequence according to Formula 2 also contains sequence to ensure its delivery into the cytosol of epithelial cells where it has its target. Such a sequence may be a cell-penetration-promoting sequence or a sequence that promotes cell surface binding to epithelial cells followed by phagocytosis into that cell.

According to certain preferred embodiments, a sequence according to Formula 2 is Formula 2a
(SEQ ID NO: 9)
$X_1$-$X_2$-$X_3$-$X_4$-$X_5$-$X_6$-$X_7$-$X_8$-$X_9$-$X_{10}$-$X_{11}$$X_{12}$,
or (SEQ ID NO: 10)
$X_1$-$X_2$-$X_3$-$X_4$-$X_5$-$X_6$-$X_7$-$X_8$-$X_9$,
or (SEQ ID NO: 11)
$X_3$-$X_4$-$X_5$-$X_6$-$X_7$-$X_8$-$X_9$-$X_{10}$-$X_{11}$-$X_{12}$, preferably (SEQ ID NO: 9)
$X_1$-$X_2$-$X_3$-$X_4$-$X_5$-$X_6$-$X_7$-$X_8$-$X_9$-$X_{10}$-$X_{11}$-$X_{12}$ wherein:
$X_1$ is up to 10 positively charged amino acid residues;
$X_2$ is a positively charged amino acid residue;
$X_3$ is Ala or Val;
$X_4$ is absent or Ala or 1, 2, 3 or 4 positively charged amino acid residues;
$X_5$ is a positively charged amino acid residue;
$X_6$ is Tyr;
$X_7$ is Gln;
$X_8$ is Tyr;
$X_9$ is absent or Ala or 1, 2, 3 or 4 positively charge amino acid residues;
$X_{10}$ is a positively charged amino acid residue;
$X_{11}$ is a positively charged amino acid residue; and
$X_{12}$ is up to 10 positively charge amino acid residues; or wherein all amino acid residues are of the D-configuration and the sequence order is reversed.

According to certain embodiments of the alternative formulae give immediately above for Formula 2a, relating to all aspects of the present invention,
$X_1$ is up to 10 residues of Lys and/or Arg in any combination;
$X_2$ is Lys or Arg;
$X_3$ is Ala or Val;
$X_4$ is absent Ala, Lys or Arg;
$X_5$ is Lys or Arg;
$X_6$ is Tyr;

$X_7$ is Gln;
$X_8$ is Tyr;
$X_9$ is Ala or Lys or Arg;
$X_{10}$ is Lys or Arg;
$X_{11}$ is Lys or Arg; and
$X_{12}$ up to 10 residues of Lys and/or Arg in any combination; or all amino acid residues are of the D-configuration and the sequence order is reversed.

According to some embodiments:
$X_1$ is Lys or Arg;
$X_2$ is Lys or Arg;
$X_3$ is Ala;
$X_4$ is absent;
$X_5$ is Lys;
$X_6$ is Tyr;
$X_7$ is Gln;
$X_8$ is Tyr;
$X_9$ is absent;
$X_{10}$ is Lys or Arg;
$X_{11}$ is Lys or Arg; and
$X_{12}$ is Lys or Arg.

According to some embodiments:
$X_1$ is Arg;
$X_2$ is Lys;
$X_3$ is Ala;
$X_4$ is absent;
$X_5$ is Lys;
$X_6$ is Tyr;
$X_7$ is Gln;
$X_8$ is Tyr;
$X_9$ is absent;
$X_{10}$ is Arg;
$X_{11}$ is Arg; and
$X_{12}$ is Lys;

that is to say the sequence is $Arg_1$-$Lys_2$-$Ala_3$-$Lys_5$-$Tyr_6$-$Gln_7$-$Tyr_8$-$Arg_{10}$-$Arg_{11}$-$Lys_{12}$ (SEQ ID NO: 4)

The invention also comprises, in certain embodiments, the retro-inverso form of the sequences given above.

Retro-Inverso Sequences

The sequences of Formula 1 and Formula 2 are derived from naturally occurring sequences. The naturally occurring sequences from which they derive have amino acid residues in the L-configuration.

Therefore, in such circumstances, according to some embodiments, the amino acids are in L-configuration.

Peptides comprising D-amino acids may be more attractive as drugs because they tend to be less susceptible to degradation in the stomach or inside cells by proteolysis. They therefore tend to be more suitable for oral administration and tend to be effective for longer periods of time.

The present invention, in its various aspects, encompasses peptides in which all amino acids are in the D-configuration and the peptide sequence order of Formula 1 and 2 (and more narrowly defined sequences falling within the scope of Formula 1 or 2 and specified above) is reversed.

For example, the invention relates to peptides having the sequence RRVEVKYDRR-NH$_2$ (SEQ ID NO: 3) wherein the residues are preferably in L-configuration and the retro-inverso sequence NH$_2$-rrdykvevrr (SEQ ID NO: 20) wherein the residues are in D-configuration. The lower case single letter amino acid code is shorthand for retro-inverso configuration. According to certain embodiments the retro-inverso configuration is preferred.

Pharmaceutical Compositions

According to a second aspect of the invention, there is provided, a pharmaceutical composition comprising a peptide according to any of the various embodiments of the first aspect of the invention, and a pharmaceutically acceptable carrier.

According to certain embodiments, the pharmaceutical composition comprises an agent to promote penetration of the peptide into the cytosol of the target epithelial cell, for example a liposome-forming agent. The presence of such an agent is especially favoured if the peptide itself lacks a cell penetration sequence, for example if it lacks the cell-penetrating peptide sequence of Formula 1a or 2a. However, agents to assist with cell penetration may, according to some embodiments, may be present regardless of the presence or absence of such sequences in the peptide according to the first aspect of the invention. According to certain embodiments a pharmaceutical composition according to the invention may comprise a peptide according to Formula 1, or the retro-inverso analogue thereof, in combination with a peptide according to Formula 2, or the retro-inverso analogue thereof.

Enteric Coatings

A pharmaceutical composition may comprise a dosage from having an enteric coating. An enteric coating is a coating applied to oral medicinal compositions such as tablets, caplet and capsules so as to control absorption so that it takes place in the small intestine. Enteric coatings are typically applied to the surface of dosage forms so that they present a stable surface in the highly acid pH of the stomach, but breakdown rapidly in the relatively more basic environment of the small intestine. Materials used for enteric coatings include fatty acids, waxes, shellac, plastics and plant fibres.

When the present invention is used in the context of delivery of a second therapeutic agent in an oral dosage across the epithelium of the small intestine, an enteric coating may be used if the therapeutic agent would otherwise be degraded in the stomach environment. Such a coating may be especially useful if the second therapeutic agent is irritating to the stomach, if it is acid unstable (for example certain azoles such as esomeprazole are acid unstable), or if the second therapeutic agent is a protein or peptide (for example insulin, GLD-1 or a derivative, or analogue thereof) which might be expected to be degraded by enzymes present in the stomach.

Accordingly, pharmaceutical compositions according to the second aspect of the invention may comprise a solid dosage form having an enteric coating and other aspects of the invention may also utilise or relate to such a coating.

Second Therapeutic Agent

According to various aspects of the invention which relate to a peptide of the invention and a second therapeutic agent, for example the pharmaceutical compositions according to the second aspect of the invention, the two components are preferably co-mixed, for example in the pharmaceutical composition so that they are presented at the epithelial surface at the same time. The peptides of the invention may be used to deliver a wide range of therapeutic agents. They may be especially relevant to the delivery of therapeutic agents which are small molecules, and also in the delivery of therapeutic agents which are peptides or proteins or nucleic acids. For example the therapeutic agent might be insulin, parathyroid hormone, calcitonin, erythropoietin, GM-CSF or growth hormone, or a siRNA or gene therapy agent. The invention also relates to the delivery of therapeutic agents which are antibodies or antibody derivatives. Should it be found that whole antibody molecules are too large to be effectively delivered in accordance with the invention, smaller versions of antibody-based technologies for example scFv molecules, camel antibodies, single change antibody fragments and domains and the like may be of particular use. All of these therapeutic could be administered either singly or in combination with other therapeutic agents following tight junction opening by a peptide of the invention. For example insulin and GLP-1 could be delivered in the same dosage form as a peptide of the invention.

Pharmaceutical Carriers

A pharmaceutical carrier (or "drug carrier") is a substance present in a pharmaceutical composition to improve the delivery, formulation, dosage or effectiveness of a drug or to assist in its preservation, blending, preparation or processing.

Epithelium

The invention in its various aspects relates to an epithelium ("epithelial surface"). This may be an in vitro or in vivo surface. Non-limiting examples include the epithelium of the large intestine, the small intestine, the rectum, the anus, the cervix, the vagina, the respiratory tract (for example trachea, bronchioles, bronchiole or larynx), the nose, the mouth and the cornea, present both in vivo and in vitro.

Immortalized cell lines of epithelial cells, for example of the epithelial cell types described immediately above are especially contemplated.

Medicaments

According to a third aspect of the invention, there is provided a peptide to the first aspect of the invention or a pharmaceutical composition according to a second aspect of the invention of use as a medicament. Both the third and fourth aspects of the invention refer to a "medicament". Said medicament may comprise a peptide of the invention or a peptide of the invention and a second therapeutic agent as described herein with reference to other aspects of the invention. This second therapeutic agent may be a peptide, small molecular entity, nucleic acid or other chemical compound. The medicament may be formulated as described herein with reference to other aspects of the invention for the treatment of a disease disorder or non-medical condition as described elsewhere herein a subject as described elsewhere herein.

Subjects for Treatment

According to certain embodiments the present invention, in all aspects relates to the treatment of subjects. Such subjects may be of any species which have an epithelium with tight junctions.

According to certain preferred embodiments, the present invention in all aspects relates to the treatment of mammalian subjects. Most preferably the present invention in all aspects relates to the treatment of human subjects of either sex and of any age (for example from birth to 1 yrs, birth to 5 yrs, birth to 12 yrs, birth to 60 yrs, birth to 80 yrs, 2 to 60 yrs, 5 to 80 yrs, 12 to 80 yrs or 16 or 18 yrs upwards).

According to certain embodiments, the present invention in all aspects relates to the treatment of human subjects in need of a therapeutic agent which is to be delivered across a mucosal membrane. The therapeutic agent may be one of the agents described elsewhere herein. The human subject, according to certain embodiments of all aspects of the invention may be a subject to whom has been administered the therapeutic agent mentioned above simultaneously or within a time-window of 15, 10, 5, 2 or 1 minutes either side of administration of the peptide or pharmaceutical composition of the invention.

Diseases for Treatment

The peptide according to the first aspect, the pharmaceutical composition according to the second aspect, or the medicament according to the third aspect may be for the treatment of a disease or disorder or other condition. According to certain embodiments, the disease or a lung disease, The delivery of poorly absorbed drugs in accordance with the invention may have the effect similar to their administration by injection. Importantly, the ability to deliver therapeutic agents to discrete epithelial locations would also result in the local delivery to the submucosal space. For these reasons, the invention may be especially suitable for treating both systemic conditions and diseases (e.g. arthritis, short-stature, etc) and also conditions and diseases that would benefit from local targeting of therapeutic agents (e.g. Crohn's disease, asthma, etc).

Non-Therapeutic Treatment

According to certain embodiments, the various aspects of the invention relate to non-therapeutic treatment of conditions, such as cosmetic skin condition, or the treatment of a person who is not medically obese but who wishes to lose weight (or maintain a healthy weight) for cosmetic purposes.

Methods of Medical Treatment

In respect of jurisdictions where methods of medical treatment constitute patentable subject matter the present invention provides a method of treatment of a disease in a subject comprising administering to said subject a pharmaceutical composition according to the second aspect of the invention, wherein the second therapeutic agent is for treatment of the disease and wherein the presence in the pharmaceutical composition of the peptide according to the first aspect of the invention improves the delivery of the second therapeutic agent across an epithelium of the subject. According to certain preferred embodiments of this aspect of the invention, the subject, rate of administration, features of the pharmaceutical composition, the peptide of the invention, the second therapeutic agent, or the disease to be treated are as described herein in reference to other aspects of the invention.

Method of Opening Tight Junctions

According to a fourth aspect of the invention there is provided a method of opening the tight junctions of an epithelial surface comprising administering an effective amount of a peptide according to the first aspect of the invention, or a pharmaceutical composition according to a second aspect of the invention to the epithelium.

This method may be an in vivo or in vitro method. In vivo methods include methods directed to the medical treatment of a subject, for example by promoting the delivery of a second therapeutic agent to the circulation of a subject by opening the paracellular administration rate of said subject's epithelium and disease to be treated may be as described herein by reference to other aspects of the invention.

Alternatively, the method of this aspect of the invention may relate to the in vivo testing in an experimental animal or human volunteer or patient of the delivery of an agent across an epithelium. For example, a second therapeutic agent as defined by reference to other aspects of the invention may be delivered across an epithelium in order to measure the efficacy of the second therapeutic agent in treating a disease or in order to assist with the subsequent measurement of pharmacokinetic (PK) parameters. In this regard the method of this aspect of the invention may relate to the measurement of a marker molecule (for example a radiolabelled marker or other imaging or contrast agent) across said epithelium.

Alternatively this aspect of the invention may relate to the in vivo opening of tight junctions of an epithelium in cell culture, for example as a cell cultured monolayer of human or animal epithelium, in order to study the properties of the epithelium or the passage of molecules (for example drug candidates) across said epithelium.

Method of Delivery

According to a sixth aspect of the invention there is provided a method of delivering an agent across an epithelial surface comprising administering said agent in conjunction with a peptide according to a first aspect of the invention or as part of a pharmaceutical composition according to a second aspect of the invention.

In various aspects of this aspect of the invention, the epithelial surface, peptide and pharmaceutical composition may be as described in reference to the various other aspects of the invention. The method may be carried out in vitro or in vivo. The agent may be a diagnostic agent, contrast agent or according to certain preferred embodiments a therapeutic agent as described herein under the heading "second therapeutic agents".

Various aspects of the present invention are described below by reference to the following non-limiting examples and figures.

EXAMPLES

Materials and Methods

Peptide Synthesis

Peptides were synthesized by (Fmoc)-SPSS (ActivoSyn peptide synthesizer) using amino acids obtained from Nova Biochem, except for isoleucine, which was obtained from Sigma Aldrich. The first amino acid was coupled to Rink Amide MBHA resin (100-200 mesh; Nova Biochem) using N,N'-diisopropylcarbodiimide. Subsequent couplings were carried out on an Activo P-11 peptide synthesizer using PyBop. De-protection was carried out using 20% piperidine in dimethylformamide. Peptides were cleaved from the resin using a mixture of trifluoracetic acid (TFA), triisopropylsilane and water (95:2.5:2.5), and then precipitated in diethyl ether. Crude product was purified by HPLC, using a Phenomenex Gemini C18 column (250×10 mm, pore size 5 µm) and a gradient mobile phase of water with 0.1% TFA and acetonitrile with 0.1% TFA using a flow rate of 2.5 ml/min. High resolution time-of-flight mass spectra were obtained on a Bruker Daltonics micrOTOF mass spectrometer using electrospray ionisation (ESI) to verify peptide identity. Purified peptides were dried by lyophilization and stored at $-80°$ C.

Cell Culture

An immortalized human intestinal epithelial cell line (Caco-2) were maintained in DMEM/F12 medium (Gibco, Paisley, UK) supplemented with 10% FBS, 2 mM L-glutamine (Gibco) 100 U/ml penicillin and 100 µg/ml streptomycin (Gibco). Caco-2 cells were seeded at a density of 7×104/well on Transwell™ (Corning, N.Y.) polyester membrane filters (12 mm diameter, 0.4 µm pore size). Re-feeding with DMEM (Life Technologies, Paisley, UK) was carried out every second day. Caco-2 monolayers with trans-epithelial electrical resistance (TEER)>350 Ω·cm2 were considered confluent and used in transport assays; fixed paddle electrodes were used to measure TEER (World Precision Instruments, UK).

In Vitro Transport Studies

Apical to basal flux of 50 mg/ml 4 kDa dextran or 50 mg/ml 70 kDa dextran (Sigma) was performed to assess the impact of PIP peptides on paracellular permeability. Apical compartment volume was 200 µl; at set times the 600 µl basal compartment volume was collected and replaced with fresh HBSS. Apical and basal compartment fluorescence was determined using a Floustar Omega microplate reader (BMG Labtech, Ortenburg, Germany). TEER measurements were made for each well immediately after HBSS replacement. After 3 hr, the apical compartment dextran and peptide solution was removed and replaced with PBS and TEER values were recorded for a further 30 min to assess monolayer recovery.

PhosphoMLC Analysis

After rinsing with ice cold PBS, Caco-2 monolayers or epithelial cells from isolated intestinal tissue were lysed in 3 µL of a protease inhibitor cocktail and 200 µL RIPA buffer and left on ice for 10 min. Isolated intestinal tissue was similarly placed in ice cold PBS for 15 min prior to maceration in a protease inhibitor cocktail and RIPA buffer, being left on ice for 10 min. All cell and tissues lysates were centrifuged at 8000 rpm for 15 min to collect the supernatant, which was stored at $-80°$ C. until use. For Western blots analysis, lysates were separated by SDS-PAGE (12%) run at 220V for 40 min and electro-transferred onto a PDVF membrane at 30V for 70 min using an XCell™ Blot module (Invitrogen). Membranes were blocked using 5% bovine serum albumin in TBS-T (2 M Tris, HCl, pH 7.5, 4 M NaCl and 0.1% Tween 20) for 1 hr. Membranes were washed with water, incubated with primary antibody (anti-myosin light chain (phospho S20) antibody or anti-myosin light chain 2) antibody overnight at 5° C., washed thrice with TBS-T, and then incubated with secondary horseradish peroxidase (HRP)-coupled antibody for 1 hr at room temperature. After washing thrice in TBS-T, HRP activity was detected by ECL (Santa Cruz).

Cell Viability Measurement

MTT assay: Cell viability was assessed using the 3-(4,5-dimethylthiazol-2-yl)-2,5-diphenyl tetrazolium bromide (MTT; Invitrogen, Paisley, UK) assay. Following exposure of cells to CPP complexes for 72 hours, 0.5 mg/ml MTT was added to the culture medium and incubated with the cells for a further 3 hours. Media was then removed and replaced with DMSO to lyse the cells. Absorbance was then recorded at 550 nm.

Microscopy

Cells were cultured on glass coverslips before the addition of CPPs, in complex with Rhodamine tagged BSA. Cells were incubated with the complexes for 2 hours then subsequently washed several times with complete medium to remove excess complexes before being fixed with 4% paraformaldehyde. Incorporation of tagged BSA into the cells was determined through confocal microscopy (Zeiss LSM 510). Levels of BSA entry were estimated through measurement of the mean fluorescence intensity of the Rhodamine tag relative to the number of cells in the field of view.

In Vivo Studies

Male Wistar rats, bred in house, were 225-275 g (approximately 6-8 weeks old) when placed on study. Rats were housed in groups of 3-5 per cage in a 12/12 hr light/dark cycle. All experiments were conducted during the light phase and carried out using a non-recovery protocol that used continuous isoflurane anesthesia. A 4-5 cm midline abdominal incision was made to expose mid-jejunum to early ileum regions of the small intestine and to provide access to the portal vein for the insertion of a cannula. Solutions of insulin (human recombinant; Sigma) and PIP peptides were prepared in 0.9% saline containing 10 mM citric acid to reduce local proteolysis and mixed 1:1 before injection using a 29-gauge hypodermic needle in a volume of 200 µL/kg (or ~50 µL, per 250 g rat). The injection site was marked with a permanent marker. The incision was closed with surgical glue. Blood draws were taken from the portal vein as well as systemic circulation over the next two hours to monitor glucose, serum insulin and endotoxin. Control treatment groups included SC injection of insulin delivered into the intestinal lumen as well as intestinal injection of PIP peptide without insulin or insulin alone in the phosphate buffered saline (PBS) formulation used for all groups. At the end of a study, a 3-5 mm region about the marked intestine segment was isolated. This tissue was lysed for biochemical assessment of MLC phosphorylation state or fixed, sectioned, and stained with hematoxylin/eosin prior to analysis read by a licensed veterinary pathologist. Subcutaneous (SC) insulin injections (20 µl/kg) were performed in the mid-scapular region and blood glucose was measured in the same manner. All experiments were performed in accordance with the U.K. Animals (Scientific Procedures) Act of 1986, the European Communities Council Directive of 1986 (86/609/EEC), and the University of Bath's ethical review procedures.

In Vivo Toxicity Testing

Since the actions of cell penetrating peptides to induce cellular damage and toxicity is a possibility (Carter, 2013#109; Kilk, 2009#110), induction of apoptosis, as a measure of early stage cell intoxication, was assessed by examining caspase-3 enzyme activity using the APT165 commercial kit as per manufacturer's instructions (Millipore, Watford, UK). Intestinal tissues were isolated 45 min after exposure to test agents administered by direct intestinal intraluminal injection. Hygromycin (150 µg/mL) was administered as a positive control to incite apoptosis through caspase-3 activation.

PhosphoMLC Analysis

After rinsing with ice cold PBS to remove PIP peptide or control treatment agents, isolated intestinal tissue was placed in ice cold PBS for 15 min prior to addition of 25 µl protease inhibitor cocktail (Fisher), 25 µl phosphatase inhibitor cocktail (Fisher) and 500 µl RIPA buffer (Sigma Aldrich). After 10 min on ice lysates were centrifuged at 8000 rpm for 15 min to collect the supernatant, which was stored at −80° C. until use. For Western blots analysis, lysates were separated by SDS-PAGE (12%) run at 220V for 40 min and electro-transferred onto a PDVF membrane at 30V for 70 min using an XCell™ Blot module (Invitrogen). Membranes were blocked using 5% bovine serum albumin in TBS-T (2 M Tris HCl, pH 7.5, 4 M NaCl and 0.1% Tween 20) for 1 h. Membranes were washed with water, incubated with primary antibody (anti-myosin light chain (phospho S19) antibody (Cell Signalling Technologies) or anti-myosin light chain 2 antibody (Abcam) overnight at 5° C., washed thrice with TBS-T, and then incubated with secondary horseradish peroxide (HRP)-coupled antibody for 1 h at room temperature. After washing thrice in TBS-T, HRP activity was detected by ECL (Santa Cruz).

Cell Viability Measurement

Induction of apoptosis, as a measure of early stage cell intoxication, was assessed by examining caspase-3 enzyme activity using the APT165 commercial kit as per manufacturer's instructions (Millipore, Watford, UK). Intestinal tissues were isolated 45 min after exposure to test agents administered by direct intestinal intraluminal injection. Hygromycin (150 □g/mL) was administered as a positive control to incite apoptosis through caspase-3 activation.

Microscopy

PIP peptide-mediated uptake of Cy3-labeled insulin (Nancocs) was evaluated in vivo where exposed intestinal segments were isolated 15 min after administration for microscopic analysis. Isolated tissues were rinse briefly in ice-cold PBS and then fixed with 4% paraformaldehyde on ice prior to assessment using a Zeiss LSM 510 fluorescence microscope. DAPI (4',6-diamidino-2-phenylindole) was used as a nuclear stain.

Data Analysis

TEER values were calculated by subtracting blank filter reading and normalized as a percentage of the initial TEER value for that monolayer. Fluorescent dextran flux used to calculate paracellular permeability was performed as previously described. Blood glucose levels were expressed as a percentage of the baseline glucose levels for each animal. Data were compared to control values using a two-tailed, un-paired Student's T-test. A p-value of <0.05 was considered to demonstrate significant differences.

Example 1—Background Theory to the Dynamic Control of Tight Junction (TJ) Structure and Function TJ structures are composed of integral membrane proteins that interact with contractile and scaffolding elements to dynamically regulate epithelial barrier properties in health and disease (Turner (2009) Nat. Rev. Immunol. 9:799-809; Xiao et al. (2011) J. Aller. Clin. Immunol. 128:549-556). Physiological and pathological stimuli alter TJ barrier properties thru multiple kinases: protein kinase C (PKC), protein kinase A, mitogen-activated protein kinases, phosphoinositide 3-kinase and Rho signalling pathways (Gonzalez-Mariscal (2008) Biochim. Biophys. Acta 1778:729-756). A central element of this kinase cross-talk involves regulating myosin light chain (MLC) phosphorylation (Woodsome et al. (2006) J. Cell Sci. 119:1769-1780); FIG. 1. A direct connection exists between increased MLC phosphorylation and decreased TJ barrier function; pro-inflammatory cytokines can drive MLC phosphorylation, resulting in the opening of TJs, with MLC kinase (MLCK) playing a pivotal role. The inventor has previously identified a membrane-permeable, stable peptide inhibitor of MLCK, termed PIK (arrow in FIG. 1) that is capable of rectifying inflammation-driven decreases TJ barrier function in the gut and lung (Clayburgh et al. (2005) J. Clin. Invest. 115:2702-2715; Mirzapoiazava et al. (2011) Am. J. Respir. Cell Molec. Biol. 44:40-52). MLCK function is presumably counterbalanced by the actions of MLC phosphatase (MLCP). While studies using genetic knock-out for targets within this network can provide insight into their role in barrier function, actions on the overall system by any molecule aimed at a single target within this network must be determined through pharmacological studies. That these protein surface contact sites are intracellular and that a primary site for relevant testing of these agents is the intestine, successful inhibitors should preferably be both stable and membrane-permeable.

Example 2—Preliminary Studies

The inventor has previously developed a 9-residue peptide (PIK) inhibitor of MLCK that closes TJ structures poised in the open position due to inflammatory events. PIK emulates a protein surface structure critical to MLCK function. Following identification of critical interfacial contacts, this peptide was modified to integrate amino acid that would allow for cell-penetrating peptide (CPP) function and increase metabolic stability. Applying these same design principles, agents and methods according to various aspects of the present invention have been developed.

Figure 3:
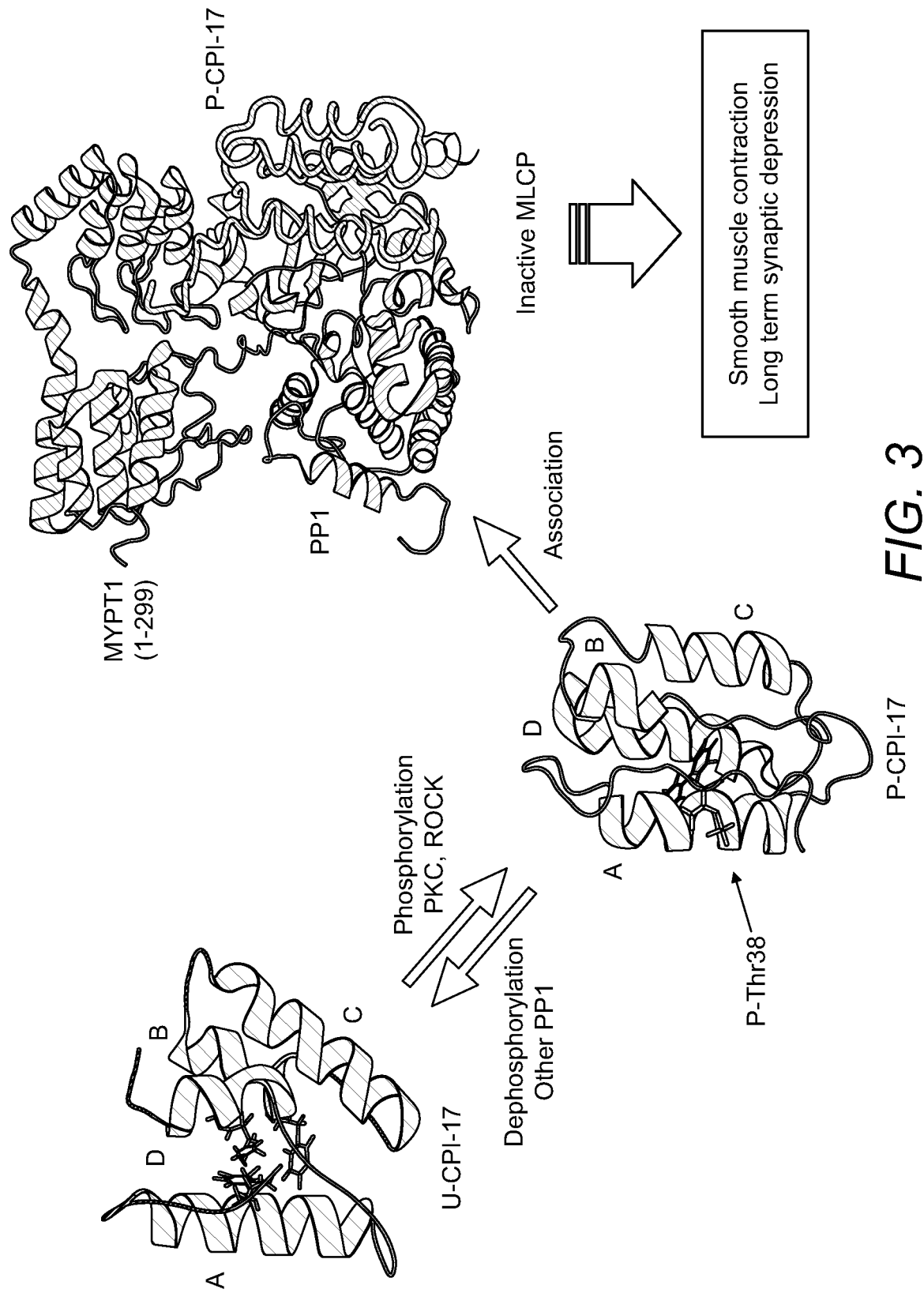
FIG. 3: Residues 1-299 of MYPT1 interact with PP1 at one surface, while CPI-17 interacts with another face. Ribbon depictions of crystal structures describe how MYPT1 and CPI-17 are projected to interact in smooth muscle cells. These interactions may differ from those polarized epithelial cells.

MLCP is a trimeric protein phosphatase-1 (PP1) holoenzyme, consisting of a PP1 isoform, the myosin targeting subunit MYPT1-CPI-17 regulatory complex, and a 21 kDa accessory subunit. To identify potential peptide MLCP inhibitors, the inventor has focused on interactions between MYPT1 or the 17 kDa protein inhibitor CPI-17 with PP1 to directly regulate MLCP function (FIG. 3).

Example 3—Targeting PP1-CPI-17 Interactions

Inhibition of MLCP by CPI-17 is driven by PKC-stimulated events; phosphorylation of residue $T^{38}$ ($pT^{38}$) in CPI-17 enhances MLCP inhibition over 1000-fold; a minimal inhibitory domain within CPI-17 was identified that includes $T^{38}$ (24) and a small cadre of peptides emulating the $R^{36}$VTVKYDRR$^{44}$ (SEQ ID NO: 13) sequence in CPI-17 that participates in its interaction with PP1 were synthesised. Included in the initial peptide set were modifications to mimic $pT^{38}$ (glutamic acid; E), and introduction of additional basic to emulate CPP sequences to enhance membrane permeability (Table 1).

Table 1. Show the results of tested CPI-17 derived peptides. $R^{36}$VTVKYDRR$^{44}$ (SEQ ID NO: 8) was selected as the starting sequence (entry 1). Residues were varied in test series (entries 2-6) as indicated (bold, underlined). Efficacy was determined by TEER reduction following apical application to Caco-2 cell monolayers.

| # | Peptide sequence | Efficacy at 5 mM |
|---|---|---|
| 1 | NH₂-RRV TVKYDRR-NH₂ (SEQ ID NO: 14) | No |
| 2 | NH₂-RRVpTVKYDRR-NH₂ (SEQ ID NO: 15) | No |
| 3 | NH₂-RRV TVKYKRR-NH₂ (SEQ ID NO: 16) | No |
| 4 | NH₂-RRVpTVKYKRR-NH₂ (SEQ ID NO: 17) | No |
| 5 | NH₂-RRK TVKYDRR-NH₂ (SEQ ID NO: 18) | No |
| 6 | NH₂-RRV EVKYDRR-NH₂ (SEQ ID NO: 3) | Yes |

Figure 4B:
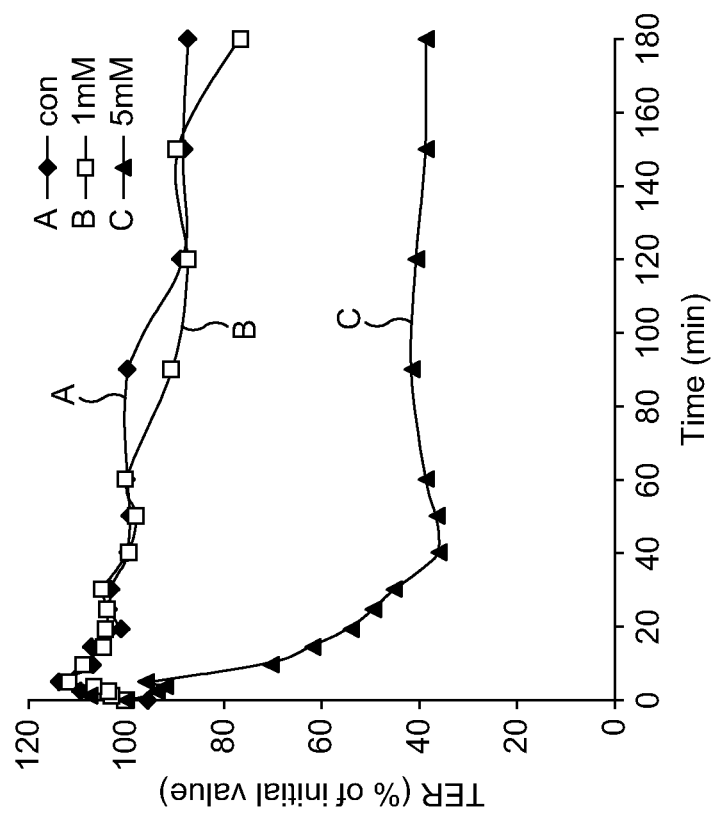
FIG. 4: [A] Time course of actions of RRVEVKYDRR (peptide 640, SEQ ID NO: 3) on TEER (trans-epithelial electrical resistance) of Caco-2 cell monolayers at 1 mM and 5 mM versus control without peptide. [B] Lack of peptide cytotoxicity up to 5 mM-MMT assay, caspase activation, etc.
Figure 4A:
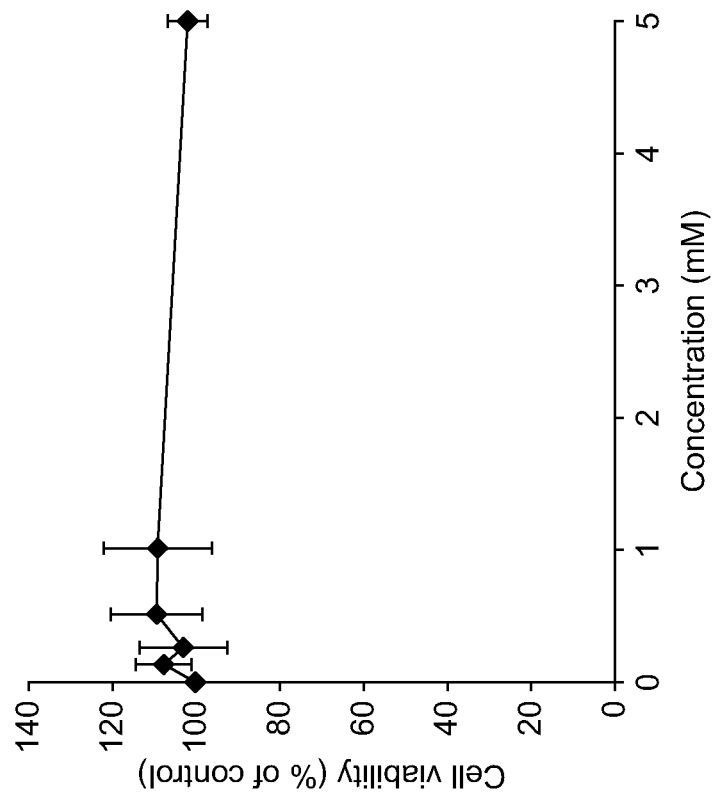

Peptides were applied apically at a concentration of 5 mM to confluent monolayers of Caco-2 cells grown on semipermeable inserts (Rubus et al. (1996) J. Pharma. Sci 85:165-169) to assess their ability to affect TJ function (Peterson & Mooseker (1992) J. Cell. Sci. 102(3):581-600). RRVEVKYDRR (peptide #6; peptide 640, SEQ ID NO: 3) reduced the trans-epithelial electrical resistance (TEER) of Caco-2 monolayers with a drop of 50% within 25 min of addition (FIG. 4), and none of the peptides were toxic at this concentration according to MTT assay (Mosman (1983) J. Immunol. Methods 65:55-63). Critically, following gentle washing, RRVEVKYDRR (SEQ ID NO: 3)-treated Caco-2 monolayers TEER values recovered to 80% of their original values within 24 h. A lead candidate, peptide NH₂-rrdyk-vevrr-NH₂, (SEQ ID NO: 20) was identified based on the RRVEVKYDRR (SEQ ID NO: 3) sequence but using the retro-inverso configuration with D-configuration amino acids.

While CPI-17 is widely expressed in smooth muscle (Eto (2009) J. Bid. Chem. 369:149-156), this data is the first to suggest its functional role in polarized epithelial cells. While $pT^{38}$ is essential for the inhibitory function of CPI-17 itself, the present findings indicate a suitable stable mimetic (e.g. E residue) can replace $pT^{38}$ for our application. The N and C termini of the peptides of table 1 are provided as cell-penetrating sequences but could be dispensed of if other methods of achieving cell penetration were employed.

Example 4—Targeting of PP1-MYPT1 Interactions

MLCP inhibition occurs following Rho-kinase mediated phosphorylation of MYPT1 at residues $T^{696}$ and $T^{853}$ (Murthy et al. (2003) Biochem. J. 374:145-155). MYPT1 binds PP1 via 3 different regions: the RVxF binding motif, the N-terminal arm and the $2^{nd}$ group of ankyrin repeats of this protein. While phosphorylation of MYPT1 at both $T^{696}$ and $T^{853}$ appears be involved in MLCP regulation, a KVKF sequence within the 300 residue N-terminal domain of MYPT1 facilitates its association with PP1 (Peti et al. (2013) FEB S.J. 280:596-611). Structural analysis of MYPT bound to PP1 shows that $E^{300}$ to $E^{309}$ of PP1 is positioned between 2 ankyrin repeats of MYPT; in particular the ankyrin repeats bind with $Y^{305}$ and $Y^{307}$, suggesting that the C terminus of PP1 is important for regulatory subunit interaction to mediate isoform specificity. It was therefore speculated that a peptide corresponding to this area could prevent MYPT binding to PP1 and hence diminish myosin specificity of the MYPT/PP1 complex.

Figure 5A:
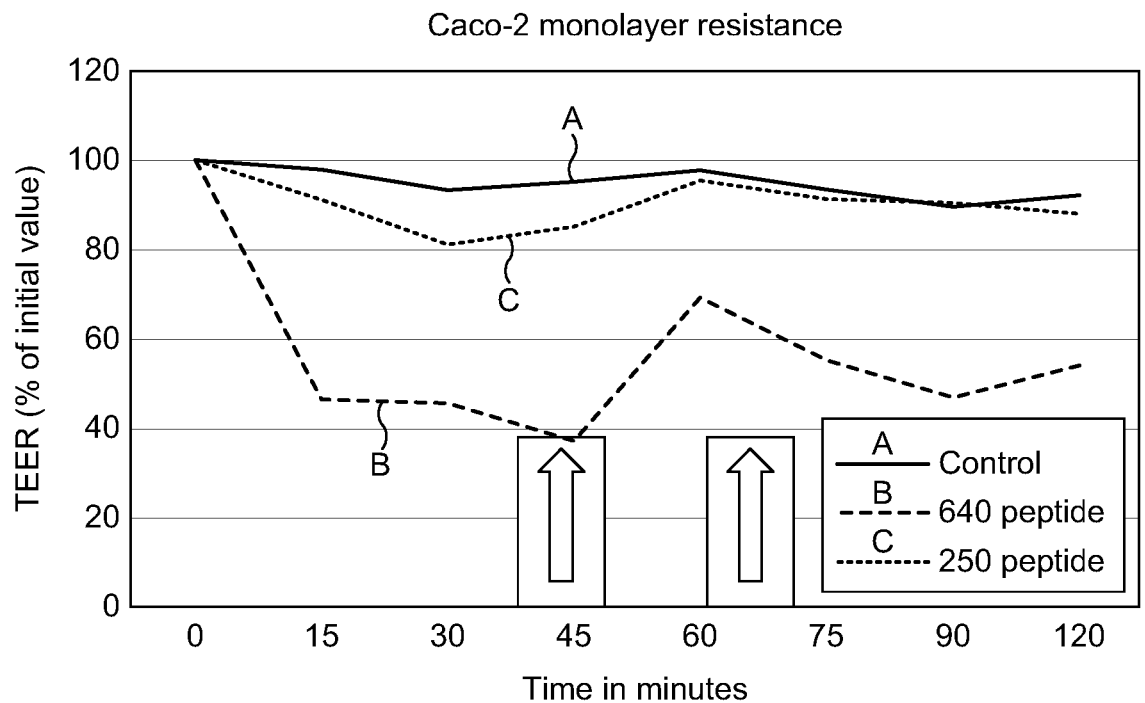
FIG. 5: Actions of RRVEVKYDRR (peptide 640, SEQ ID NO:3) and RKAKYQYRRK (peptide 250, SEQ ID NO:4) versus a control peptide (all added at 5 mM) on TEER [left] and 4 kDa fluorescein-labeled dextran (4FD) transport [right]. Measurements were made at 0, 15, 30, 45, 60, 75, 90, and 120 min. At 45 min all apical medial were replaced with 4FD but no peptide. At 70 min all apical media were replenished with 4FD plus the same peptide present prior to washout. Each time point value represents the mean of two Caco-2 monolayers; no statistical analysis was performed.
Figure 5B:
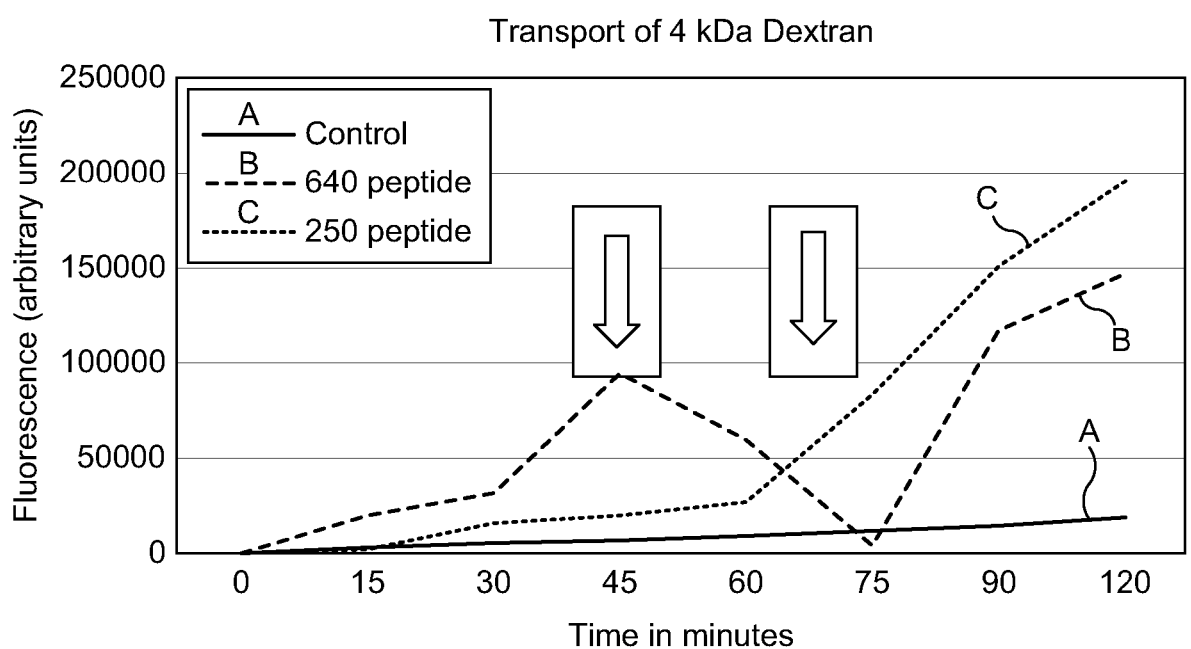

To test this hypothesis RKAKYQYRRK (peptide 250, SEQ ID NO: 4) was synthesized that incorporated the $^{301}$KAKYQY$^{306}$ (SEQ ID NO: 19) region of the C-terminal region of PP1. Assessment of the targeted inter-facial contacts suggested one could add an R residue and the tripeptide RRK at the N- and C-termini, respectively, without interfering with function to facilitate CPP function. Since polycations can induce cellular damage and toxicity (Wender et al. (2005) Org. Lett. 7:4815-4818), a lack of cytotoxicity for this peptide was confirmed using the MTT assay (data not shown). Apical addition to polarized Caco-2 monolayers of 5 mM peptide 250 was compared to that of 5 mM RRVEVKYDRR (peptide #6; peptide 640, SEQ ID NO: 3) and a control peptide (FIG. 5). While peptides 250 and 640 both increased transport of a paracellular marker relative to the control, they did so over different time courses and with different impacts on TEER. The inventor selected 4 kDa fluorescent dextan (4FD) as the paracellular marker as the hydrodynamic radius of this molecule is slightly larger than that for insulin and GLP-1 and thus should predict their transport. Peptide 640, which targeted PP1-CPI-17 interactions, caused a rapid decreased in TEER to ~50% of its initial value and caused an almost immediate increase in 4FD transport; these effects were tightly coupled to peptide washout at 45 min and re-addition at 70 min. Peptide 250, which targeted PP1-MYPT1 interactions, produced a slower and less pronounced drop in TEER and less prominent initial increase in 4FD transport compared peptide 640. Interestingly, while removal of peptide 250 at 45 min caused a recovery of TEER, re-addition of the peptide at 70 min failed to affect TEER but further enhanced 4FD transport.

Based upon this information a lead candidate, peptide 250=NH₂-krryqykakr-NH₂ (SEQ ID NO: 21), which uses the retro-inverso configuration and D-amino acids, was identified.

These studies demonstrate that peptides rationally designed to block interactions of CPI-17 or MYPT1 with PP1 can produce distinct pharmacological outcomes with regard to TEER and paracellular transport, suggesting that separate regulatory mechanisms are present, involving CPI-17 and MYPT1, which allow TJs to open dynamically to varying extents and rates.

In Vitro Studies

Figure 6A:
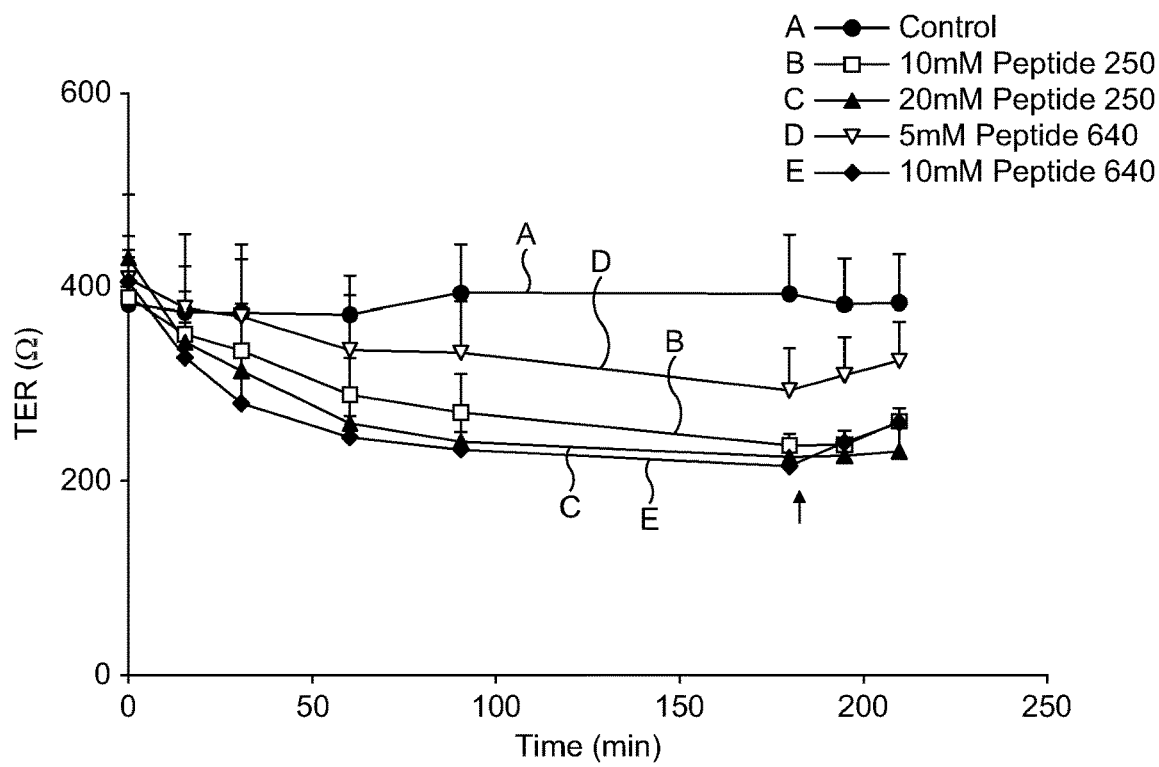
FIG. 6: (A) Absolute TEER and (B) % of initial TEER across Caco-2 monolayers following application of peptide 250 or peptide 640. Arrow represents point when peptide was washed of and replaced with PBS. Control is PBS with no peptide. n=6 for control and n=5 for all peptide groups. Data shown are means±SD.
Figure 6B:
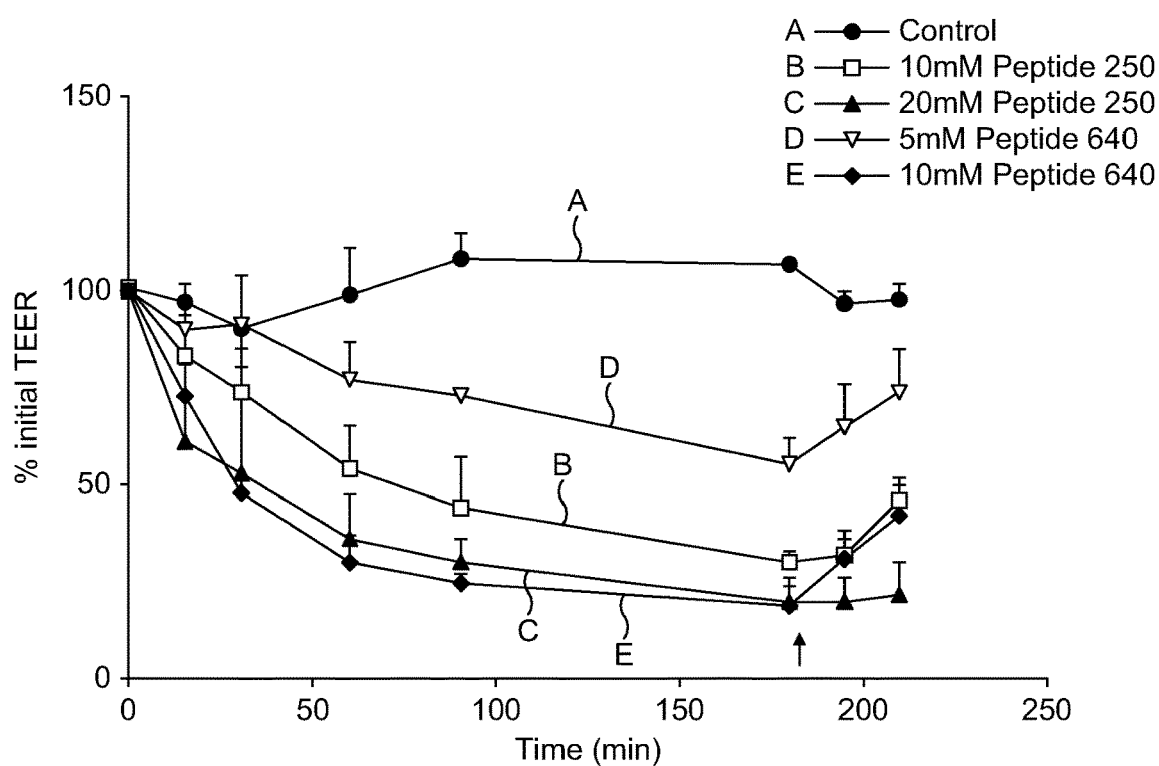

In order to adequately compare PIP peptides 250 and 640, we attempted to match the two based on response based upon TEER. This was done because of several uncertainties that make a direct dose comparison inappropriate because it is likely that the two peptides have different properties critical to their actions: accessibility to their intracellular targets (due to differing CPP capabilities), binding affinities for their respective MLCP-related targets, off-target actions, and intracellular stabilities. We determined that 20 mM peptide 250 provided a very comparable response to 10 mM peptide 640 (FIG. 6). Reducing the apical dose of these two PIP peptides demonstrated that each induced dose-dependent changes in TEER with regard to both rate of onset and maximum effect (FIG. 6). After 180 min of PIP peptide exposure, replacement of fresh media to the apical compartment showed that removal of these PIP peptides initiated a rapid reversal of TEER depression with cells exposed to peptide 640 possibly responding more rapidly than those exposed to peptide 250 (FIG. 6). This observation suggests that recovery of the cell alterations induced by peptide 250 may be less dynamic than pathways affected by peptide 640. Since peptide 640 was designed to affect a PKC-mediated regulator of MLCP and peptide 250 was designed to affect a Rho-kinase-mediated regulation of MLCP, such a suggestion is consistent with the perceived roles played by PKC and Rho-kinase in the rapid and more durable alterations of TJ structure/function.

Figure 7A:
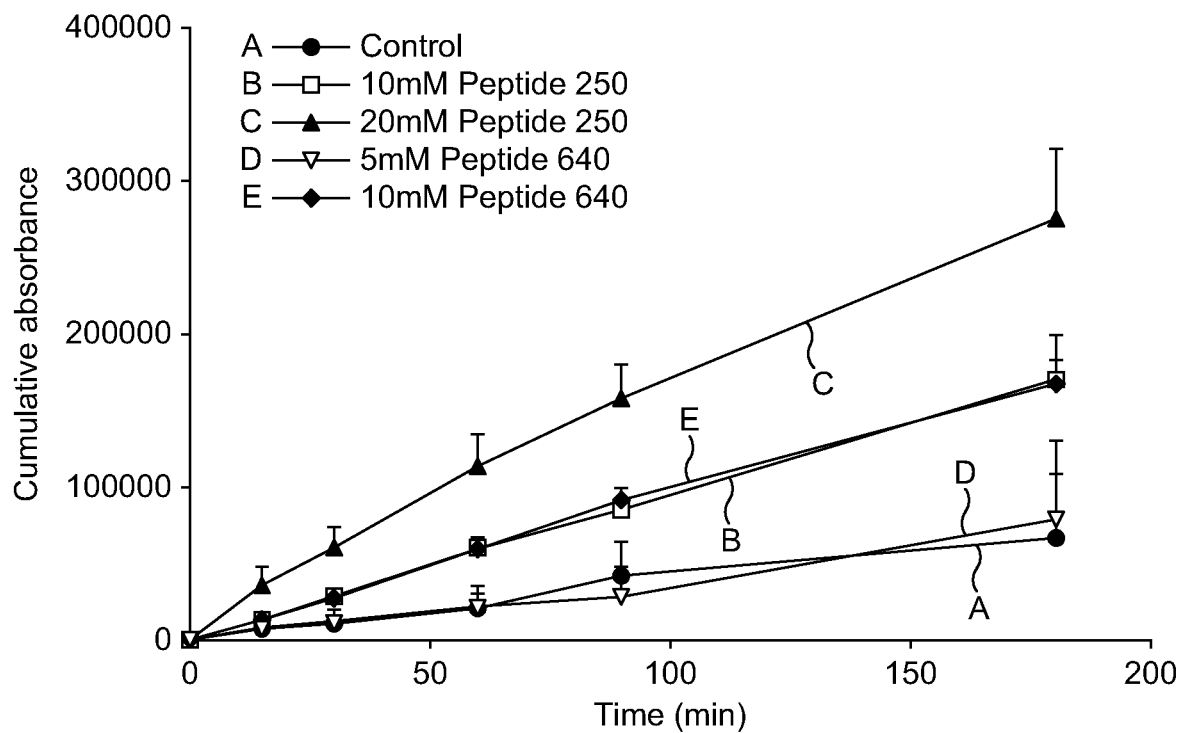
FIG. 7: Cumulative amount of (A) 4 kDa and (B) 70 kDa dextran that was found in the baso-lateral compartment following application of dextran with peptide 250 or peptide 640. n=6 for control and n=5 for all peptide groups. Data shown are means±SD.
Figure 7B:
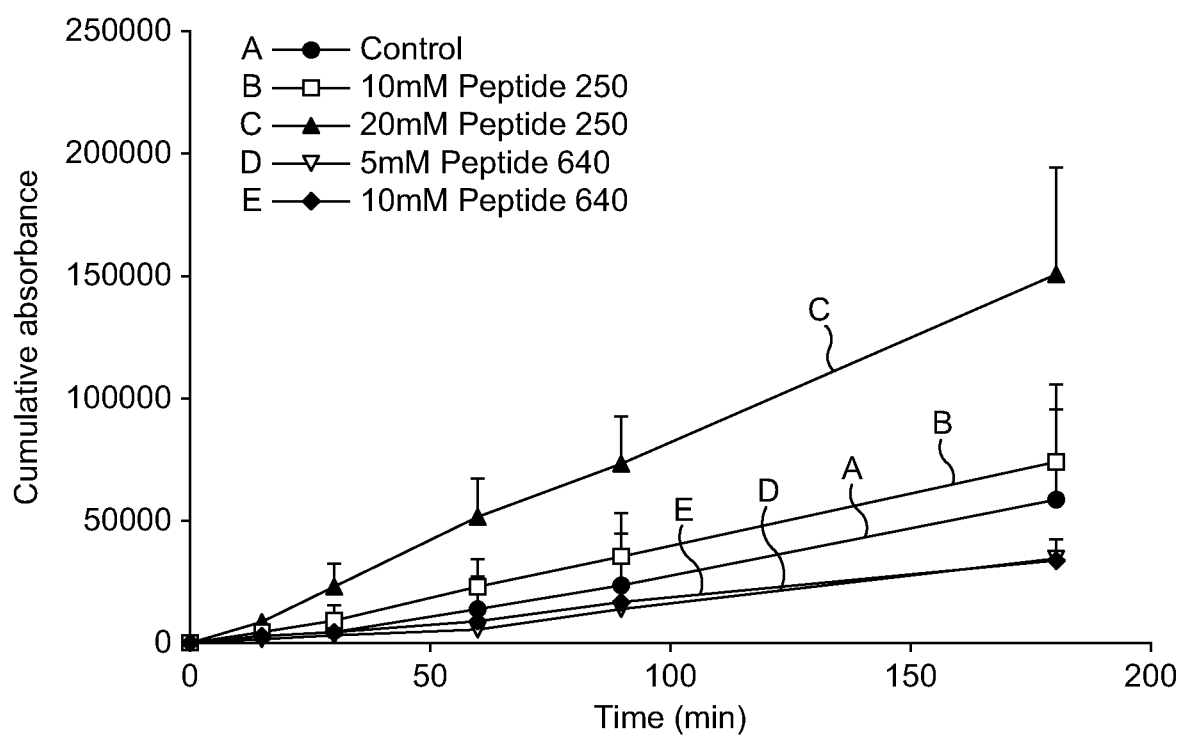

We next asked if the actions of PIP peptides 640 and 250 on TEER values translated to changes in paracellular permeability (FIG. 7). Despite producing a nearly 50% loss in TEER after 180 min of exposure, 5 mM of peptide 640 failed to affect the permeability of 4 kDa dextran across Caco-2 monolayers. Apical application of 10 mM peptide 640 increases the rate of 4 kDa permeation by ~3-fold. Interestingly, 10 mM peptide 640 was equal to 10 mM peptide 250 with regard to 4 kDa flux rates; despite have a slightly delayed and less intense impact on TEER changes compared to this other peptide. Strikingly, 20 mM peptide 250 resulted in twice the flux rate (~6-fold compare to control) for 4 kDa dextran compared to 10 mM peptide 640 even though the TEER change profiles were nearly identical for these treatments. We also observed that peptide 640 failed to affect the flux of 70 kDa dextran while peptide 250, at 20 mM, could increase this flux ~3-fold. The linearity of these enhanced fluxes of 4 kDa dextan (FIG. 7) suggested that the actions of permeability changes induced by these PIP peptide was quite rapid despite the time required to achieve a plateau of TEER response (FIG. 6). There was a hint of a slightly delayed induction of enhanced 70 kDa dextran transport induced by 20 mM peptide 250. Overall, these results suggest that peptide 640 induces a more dynamic and less robust opening of the paracellular route compared to equivalent actions (based upon TEER) induced by peptide 250.

In Vivo Studies

Figure 8A:
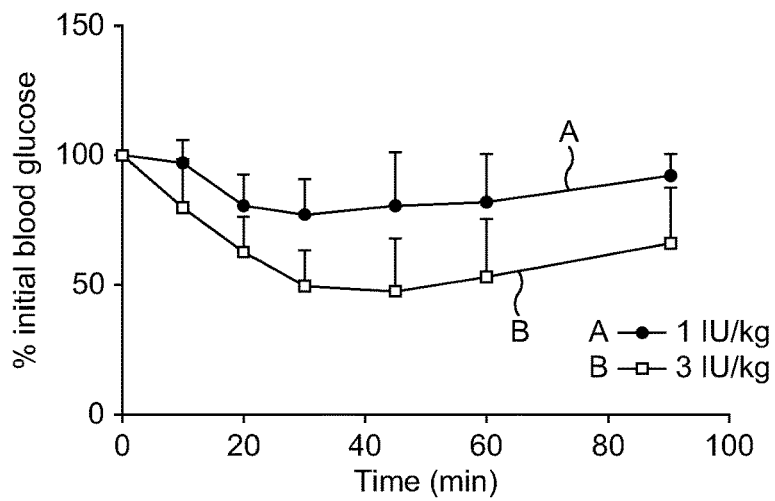
FIG. 8: (A) % initial blood glucose following S.C. injection of insulin in male Wistar rats. % initial blood glucose levels following intra-intestinal injection of 30 IU/kg insulin with (B) peptide 250 and (C) peptide 640. n=3 for all data sets. Data shown are means±SD.
Figure 8B:
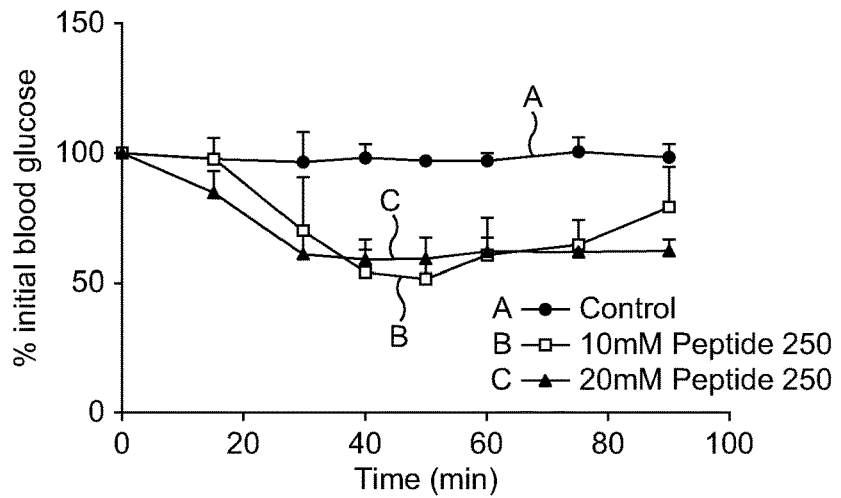

Our focus was to examine intestinal epithelial transport prior to addressing formulation challenges related to bypassing stomach acids and pancreatic enzymes; such challenges can be solved with established pill or tablet technologies but require higher order animal models than rodents. Presently, we used a rat model where small (50 µL) volume was directly injected into the lumen of the small intestine, in particular distal jejunum to proximal ileum. We calibrated the responses achieved by oral delivery by subcutaneous (SC) injection of insulin; a dose-dependent decrease in blood glucose that reached its nadir by ~30 min and began to recover by ~90 min. SC injection of 3 IU/kg produced ~50% decrease in blood glucose (FIG. 8a). Direct intraluminal injection into the small intestine (mid-jejunum to mid-ileum) of rats of 30 IU/kg had no effect on blood sugar (FIG. 8b). ILI of 30 IU/kg of insulin plus 10 mM peptide 250, however, resulted in a blood glucose drop and recovery profile similar to that observed for the SC injection of 3 IU of insulin, noting that 70-80% blood sugar recovery had been achieved by 90 min (FIGS. 8a, b). Interestingly, 20 mM peptide 250 administered with 30 IU/kg by ILI resulted in a 40% drop in blood glucose by 30 min that remained at this level for the remainder of the experiment (FIG. 8b). Direct ILI of 30 IU/kg of insulin with 10 mM peptide 640 resulted in much delayed decrease in a blood glucose change profile (FIG. 8c) relative to SC injection (FIG. 8a) or 10 mM peptide 250 (FIG. 8b); ILI of 20 mM peptide 640 was required to produce a similar effect as that observed with 10 mM peptide 250.

These results are intriguing as they suggest that these PIP peptides have distinct in vitro and in vivo response profiles that may be related to the durability of their response. In vitro the applied PIP peptide remains present and functional until it is physically removed. In vivo, however, the effective concentration of a PIP peptide at the luminal epithelial surface is complicated by events such as luminal flush and systemic absorption; events that might alter the amount and duration of time a PIP peptide may be in the cytoplasm of a small intestinal epithelial cell. We observed that peptide 640 appeared to induce more dynamic responses for TEER than peptide 250, which would result in more durable responses in vivo.

Mechanism of PIP Peptide Actions

Figure 8C:
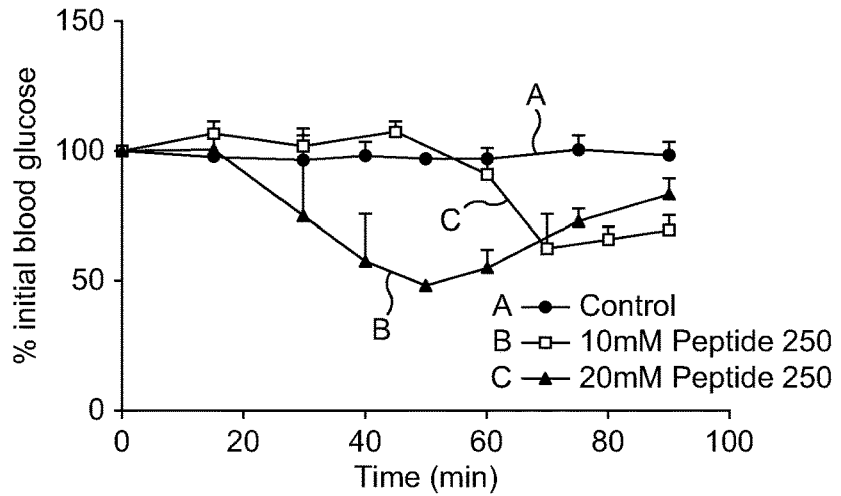

These in vivo results are, in general, consistent with our in vitro studies performed using the human intestinal epithelial cell line Caco-2 that suggested a dynamic alteration in paracellular permeability (FIGS. 6 & 7). As anticipated, the actions of these PIP peptides in vivo were transient and the duration and time onset of their actions was dose-dependent. Differences between PIP peptides 250 and 640 were readily apparent in vitro where their absolute concentration and duration of exposure could be controlled. We examined the onset and duration of PIP peptides 250 and 640 actions in vivo by determining the phosphorylation status of MLC by comparing the extent of phosphoserine at position 19 of MLC (pMLC) to total MLC in rat intestinal tissue isolated from the sites of PIP peptide exposure over the time course of blood sugar measurements (FIGS. 8B & 8C).

Figure 9A:
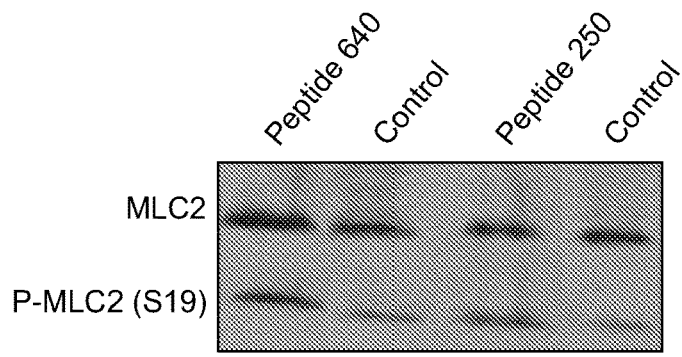
FIG. 9: Intraluminal intestinal injection of PIP peptides transiently increases pMLC content and enhances paracellular uptake of insulin in non-diabetic rat intestinal tissue in vivo. (A) Representative semi-quantitative Western blot analysis used to assess changes in the extent of myosin light chain (MLC) phosphorylated at $Ser^{19}$ ($pMLC-Ser^{19}$) relative to total MLC content. (B) ILI injection of PIP peptides increases pMLC content. Ratios of MLC to $pMLC-Ser^{19}$ levels in rat intestinal tissue at selected time points following apical application of PIP peptides at designated concentrations. *p<0.05. (C) Paracellular transport of fluorescent (Cy3-labeled) insulin enhanced by PIP peptides following ILI injection. Nuclei are DAPI-stained (blue).
Figure 9B:
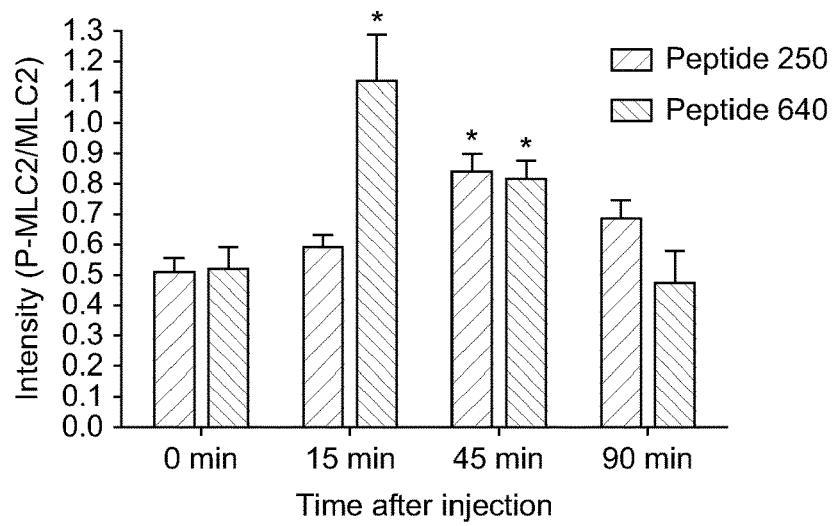

The ratio of total MLC to pMLC was assessed by semi-quantitative Western blot analysis (FIG. 9A). This analysis demonstrated that the MLC phosphorylation ratio induced by 20 mM peptide 640 was significantly increased by 15 min and remained elevated at 45 min before returning to initial levels at 90 min. The MLC to pMLC ratio profile achieved with 20 mM peptide 250 showed no significant changes at 15 min but was elevated at 45 min before returning to basal levels at 90 min (FIG. 9B). These results correlated well with the time course of blood sugar depression induced by the co-administration of these PIP peptides with insulin (FIGS. 8B & 8C). It is important to note that, while care was taken to isolate MLC from only the intestinal epithelial cells, the extraction procedure used could have resulted in some MLC isolated from other cells present in these isolated intestinal tissues.

Figure 9C:
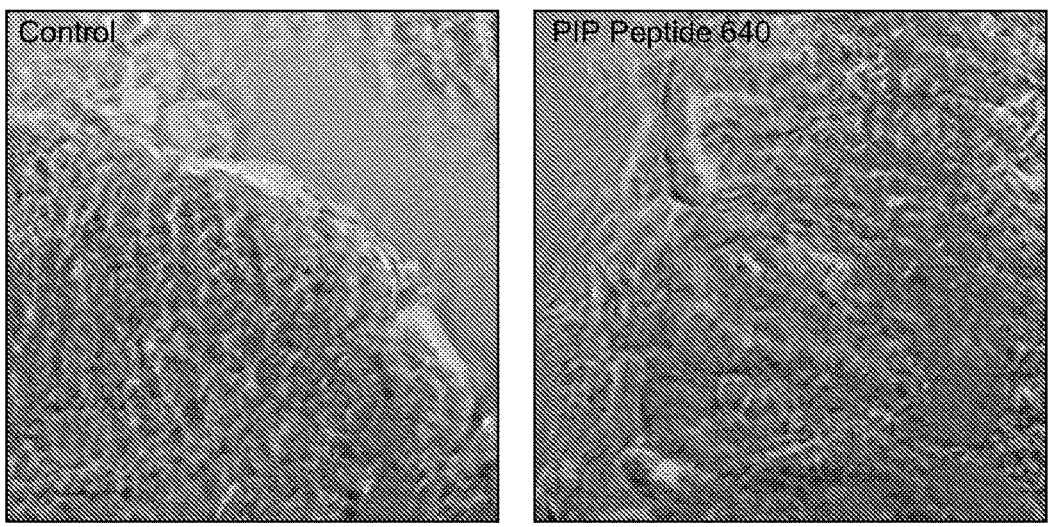

We probed our hypothesis of the PIP peptide mechanism of action further by examining the fate of a fluorescent-labeled form of insulin following its ILI injection. Fluorescent (cy3-labeled) insulin was observed in the intestinal paracellular space only when co-administered with a PIP peptide without gross anatomical modification of the epithelium (FIG. 9C). Together, these results support the hypothesis that apical, topical application of PIP peptides act locally to increase paracellular permeability of rat intestinal epithelium in vivo. Further, the time course of increase paracellular permeability of insulin was consistent with the role of a transient increase of pMLC content in epithelial cells.

Fate of PIP Peptide Enhanced Uptake of Insulin

Figure 10A:
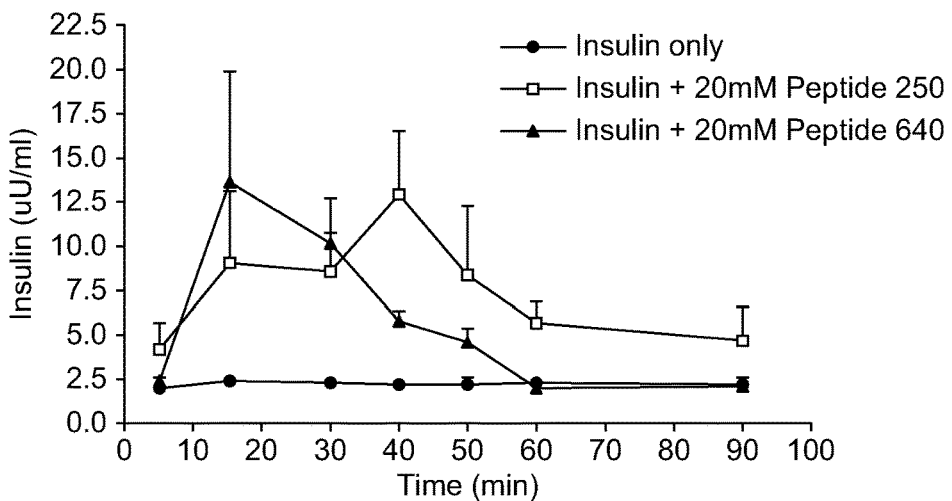
FIG. 10: PIP peptides 250 and 640 enhance the uptake of human insulin with different kinetics from the intestinal lumen of non-diabetic rats. (A) Time-concentration profiles of insulin in serum samples from blood collected from the portal vein following ILI injection of PIP peptides with 30 IU/kg of insulin. One-way ANOVA shows data sets are significantly different from each other (p<0.01). Bonferroni post-tests show that insulin with peptide 250 (p<0.01) and insulin with peptide 640 (p<0.05) were significantly different from insulin only. (B) Time-concentration profiles of insulin in serum samples collected from the tail vein following ILI injection of PIP peptides with 30 IU/kg of insulin. There was no significant difference between the groups when compared using one way ANOVA (C) Time-concentration profiles of insulin in in serum samples of blood collected from the tail and portal veins of non-diabetic mice following a SC injection of 3 IU/kg of human insulin. Data are means±SD for n=3 for each treatment group.
Figure 10B:
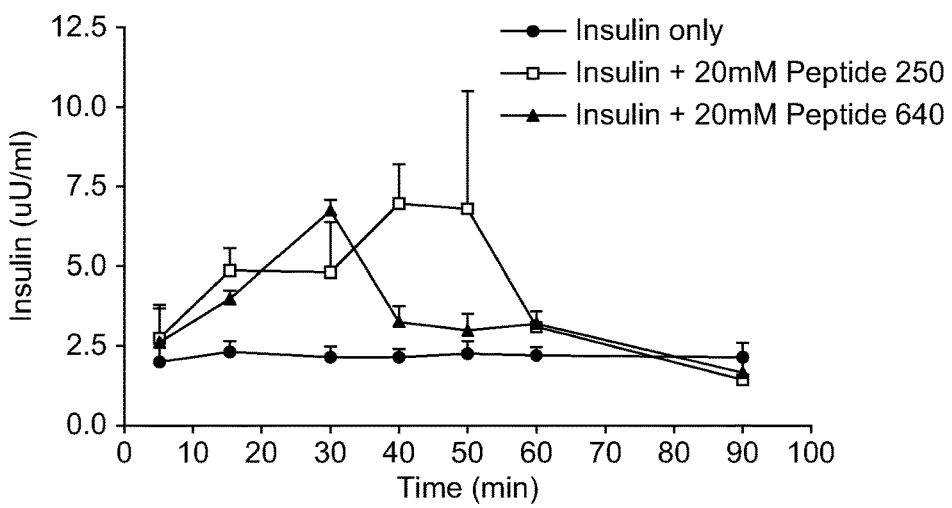

Time course studies monitoring blood glucose depression and alterations in MLC phosphorylation relevant to total MLC cell content following ILI injection of PIP peptides and 10 IU of insulin suggest an in vivo event window of approximately 30-60 min. To explore this further, we measured serum insulin concentrations in blood collected from the portal vein (FIG. 10A) and the tail vein (FIG. 10B) from 5 to 90 min following ILI. The onset of increased insulin levels and the duration of those increased levels in the portal vein suggested peptide 640 to incite a more rapid onset of action and shorter duration of action compared to peptide 250, consistent with the time course for phosphorylation ratio changes for these two peptides (FIG. 9).

Figure 10C:
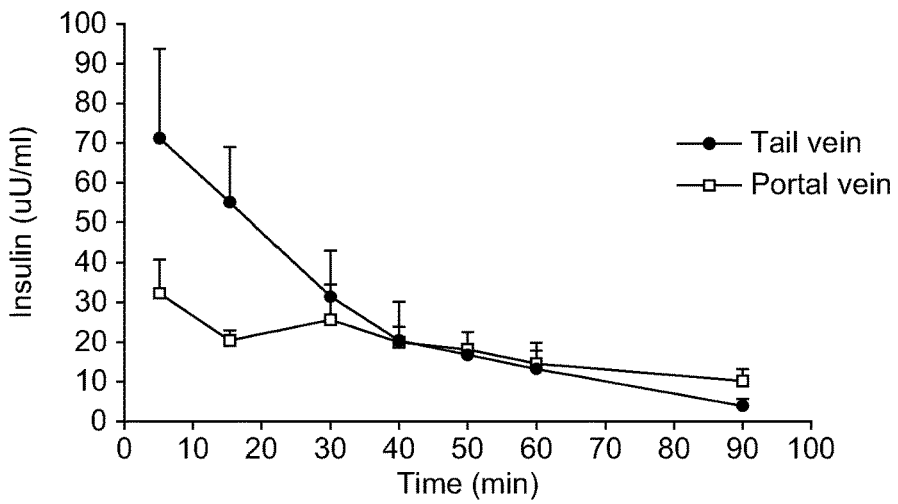

The total amount of insulin detected by ELISA in the portal and systemic (tail vein) after ILI of 10 IU/kg showed slightly different profiles following enhanced uptake by peptide 250 versus peptide 640 for the conditions tested here. Additionally, we determined time-concentration profiles for portal and systemic concentrations of insulin following SC injection (FIG. 10C). Using a non-compartmental analysis and Wagner-Nelson deconvolution, the relative bioavailability of oral administration (relative to SC) for human insulin detected in the portal vein when administered by ILI with peptide 250 versus peptide 640 were 4% and 3%, respectively. Interestingly, the relative bioavailability for human insulin reaching the systemic circulation following ILI administration with peptide 250 versus peptide 640 was 1.6% and 1.4%, respectively. These results suggested that a substantial fraction of human insulin delivered to the portal vein did not reach the systemic circulation.

Epithelial Cell Viability Following PIP Peptide Exposure

Figure 11:
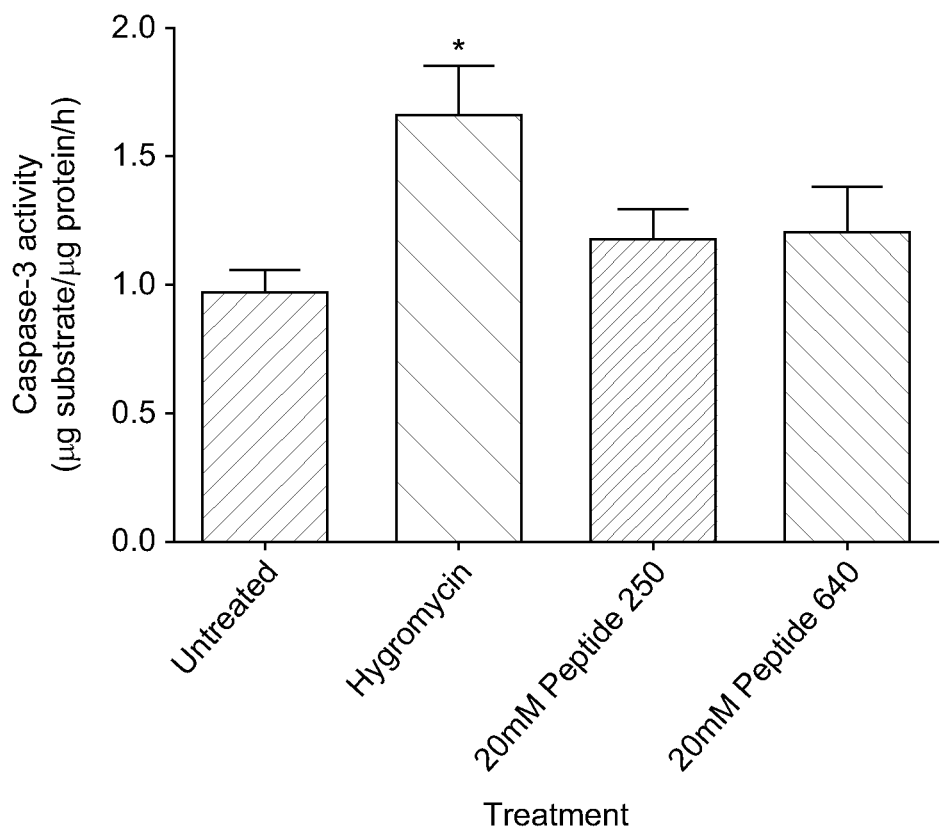
FIG. 11: PIP peptides 250 and 640 enhance the uptake of human insulin with different kinetics from the intestinal lumen of non-diabetic rats. (A) Time-concentration profiles of insulin in serum samples from blood collected from the portal vein following ILI injection of PIP peptides with 30 IU/kg of insulin. One-way ANOVA shows data sets are significantly different from each other (p<0.01). Bonferroni post-tests show that insulin with peptide 250 (p<0.01) and insulin with peptide 640 (p<0.05) were significantly different from insulin only. (B) Time-concentration profiles of insulin in serum samples collected from the tail vein following ILI injection of PIP peptides with 30 IU/kg of insulin. There was no significant difference between the groups when compared using one way ANOVA (C) Time-concentration profiles of insulin in in serum samples of blood collected from the tail and portal veins of non-diabetic mice following a SC injection of 3 IU/kg of human insulin. Data are means±SD for n=3 for each treatment group.

Initial in vitro studies using Caco-2 cells suggested that peptide 250 and 640, tested at concentrations that modulated TEER and paracellular permeability, did not affect cell viability as assessed by the mitochondrial membrane polarity marker MTS. Due to the transient nature of PIP actions in vivo, we focused on cell signals that might better define early cellular changes that could correlate with decreased cell viability; activation of the caspase enzyme cascade is an early step in apoptosis events in epithelial cells. We measured the level of caspase-3 activity in rat intestinal tissue isolated 60 min after apical exposure of peptides 250 or 640 at concentrations shown to decrease blood glucose (FIG. 8), increase the extent of pMLC (FIG. 9), and enhance the uptake of insulin into the portal vein (FIG. 10). Intestinal tissues failed to show an induction of caspase-3 enzyme activity following similar apical exposure of 20 mM PIP peptide 250 or 640, while hygromycin (150 mg/mL) administered by ILI was used as a positive control for the induction of caspace-3 did result in increasing this enzyme activity (FIG. 11). The concentration of endotoxin in portal vein blood was measured following injection of 20 mM PIP peptide 250 or 640 with insulin or insulin alone. No difference was observed between the treatments.

CONCLUSIONS

A number of agents have been explored to increase intestinal paracellular flux for the purposes of enhancing the oral delivery of biopharmaceuticals; quillaja saponin, dipotassium glycyrrhizinate, 180-glycyrrhetinic, sodium caprate, taurine, and alkylmaltosides are just a few of the agents that have been described. In general, these agents are typically screened using in vitro cell systems such as Caco-2 monolayers or isolated intestinal tissues. Some of these agents, like palmitoyl carnitine, initially show promise but ultimately their benefits are correlated with lytic effects on the cell membrane and reduced cell viability. Sodium caprate, a medium chain fatty acid present in human milk, has been even been approved as an absorption-enhancing agent in a rectal ampicillin suppository. While caprate was shown to cause TJ dilations to enhance paracellular permeability in vitro, the efficacy of caprate in vivo for its actions in man are better correlated with non-specific damage to the rectal mucosa than paracellular permeability modification. At present, there are no approved agents designed to enhance paracellular transport of a biopharmaceutical following oral delivery.

Toxicity, primarily based upon an uncertainty of their mechanism of action (or actions), seems to be a central element that limits the identification of agents to safely enhance paracellular transport of a biopharmaceutical following oral delivery. With this in mind, recent studies have suggested that caprate can alter expression of the TJ component tricellulin, to increase paracellular flux through tricellular contracts in the epithelium. This finding may explain the in vitro benefit of caprate as it is similar to the possible increase in paracellular uptake in vitro and in vivo induced by a peptide that emulates an extracellular loop domain of the TJ protein claudin 1. Therefore, methods to selectively disorganize tri-cellular TJ contacts may provide a potential mechanism of action to safely and effectively increase paracellular permeability. We have taken one such approach to identify an agent with a defined mechanism of action that could transiently open intestinal TJs to enhance the paracellular uptake of a biopharmaceutical. Our approach is based upon findings made initially by Papenheimer that demonstrated intestinal epithelium top have an endogenous nutrient-activated mechanism to increase paracellular permeation of solutes. Subsequent studies showed that this increase in paracellular permeation was due to an increase in myosin light chain (MLC) phosphorylation.

Validation of MLC phosphorylation in controlling TJ-mediated solute permeability was initially validated using a rationally designed, stable, membrane permeable inhibitor of MLC kinase (PIK) peptide that was shown to be effective in models of chronic epithelial inflammation. Presently, our goal was to identify membrane-permeable, stable, selective inhibitors of MLC phosphatase (MLCP) that counterbalances the actions of residual MLC kinase activity (FIG. 12). We used well-established principles to identify short peptide sequences capable of selectively modulating protein-protein interactions with the goal of emulating interfacial contacts involving MLCP regulatory proteins: CPI-17 and MYPT. MLCP regulation by these regulatory elements provides epithelial cells with at least two distinct mechanisms of controlling MLC phosphorylation and thus altering TJ functional properties. Peptides that have extensive interfacial contact sites sufficient to achieve target specificity suffer from poor membrane permeability and are further limited peptidase-mediated catabolism in the intestinal lumen and in the cytoplasm of epithelial cells. We designed and tested sets of peptides that emulated endogenous sequences to increase specificity that were prepared from D-amino acids for increased stability and contained an increased positive/negative charge ratio to increase membrane permeability.

Recent studies have validated the approach of using stable, membrane permeable peptides to disrupt an interfacial contact site and alter protein phosphatase 1 in living cells. As previously shown for MLPC modulation with a membrane-permeant peptide designed to target the RVxF-type PP1-binding motif and other cell membrane penetrating peptides, the PIP peptides examined in our studies did not show any cytotoxic actions in vitro or in vivo. This is in striking contrast to microcystins, a class of cyclic heptapeptide hepatoxins that inhibit multiple PP1 along with other Ser/Thr protein phosphatases by binding to a common site; illnesses associated with microcystin intoxication are related to non-specific actions resulting from increased phosphorylation of many proteins. Our results demonstrate the feasibility of enhancing the oral uptake of biopharmaceuticals by selectively inhibiting MLCP activity by targeting interfacial contacts between MLCP and specific regulatory proteins that do not induce cytotoxicity, possibly due to their specific actions.

Investigations over the last 20 years have demonstrated $Ca^{2+}$/calmodulin to activate MLCK activity while Rho kinase and protein kinase C regulate MLCP through MYPT1 and CPI-17, respectively. PIP peptide 250 had less dynamic actions and opened TJ structures to transport larger solutes when compared to the actions of peptide 640. This data suggests that suppression of MLCP through a Rho kinase-related mechanism results in a more durable and extensive modification of TJ function than those mediated by CPI-17 (FIG. 12). These studies are consistent with the possibility that Rho A may mediate slow, durable TJ changes through its actions on MYPT1 while PKC actions on CPI-17 may provide a mechanism for more rapid and dynamic changes in TJ function. Differences in the actions of PIP peptides 250 and 640 were more readily apparent in in vitro studies where their concentration and continued exposure could be controlled. In vivo studies were consistent with observations made in vitro regarding the dynamic nature of PIP peptide actions, but not as readily obvious. This was likely due to the added variability of conditions experienced in vivo.

The PIP peptides identified and tested in these studies have provided a proof of principle outcome to support several concepts regarding the regulation of MLC phosphorylation. 1) Peptides designed to disrupt protein-protein interactions between PP1 and its regulatory proteins CPI-17 and MYPT1 can transiently increase MLC phosphorylation. 2) Increased MLC phosphorylation induced by these peptides can increase the paracellular flux of macromolecules, 3) Regulation of paracellular permeability changes induced by these peptides designed to disrupt protein-protein interactions between PP1 and its regulatory proteins CPI-17 and MYPT1 is rapid and reversible. 4) Changes in MLC phosphorylation associated with these dynamic effects on paracellular barrier properties are not associated with or lead to cell toxicity. This last point is important in the consideration of next steps. While the PIP peptides 640 and 250 are effective, apparently specific, and non-toxic, the concentrations required for their function is in the mM range. This is actually not a significant issue since achieving these concentrations at local, topical applications where a biopharmaceutical is positioned simultaneously is readily achieved. Optimization of these PIP peptides to decrease the concentration required is one area of future interest. Such an effort will require multiple and iterative efforts to minimize the peptide structure while retaining target specificity and actions as well as increasing the efficiency of membrane permeability to reach the required intracellular target. These efforts may benefit from the use of stable phospho-amino acid analogues rather than the use of negatively charged amino acids to emulate these required functional elements.

Overall, our studies demonstrate that peptides rationally designed to block interactions of CPI-17 or MYPT1 with PP1 (MLCP) can produce distinct pharmacological outcomes with regard to TEER and paracellular transport. While CPI-17 is widely expressed in smooth muscle, this data is the first to suggest its functional role in polarized epithelial cells. Additionally, our results suggest that separate regulatory mechanisms may exist that allow CPI-17 and MYPT1 to open TJs dynamically to varying extents and rates. Finally, we have shown that manipulation of MLCP function using peptides designed to increase MLCP activity can be applied to the pharmaceutically relevant issue increasing the oral bioavailability of insulin.

The invention claimed is:

1. A peptide comprising the amino acid sequence Arg-Arg-Asp-Tyr-Lys-Val-Glu-Val-Arg-Arg (SEQ ID NO: 20), wherein all residues of SEQ ID NO:20 are in D-configuration.

2. A peptide as claimed in claim 1, wherein the C-terminus is amidated.

3. A pharmaceutical composition comprising a peptide of claim 1 and a pharmaceutically-acceptable carrier.

4. A pharmaceutical composition as claimed in claim 3 further comprising a therapeutic agent.

5. A pharmaceutical composition as claimed in claim 4, wherein said therapeutic agent is insulin, or a derivative, analogue or mimic thereof.

6. A pharmaceutical composition as claimed in claim 4, wherein said therapeutic agent is GLP-1, or a derivative, analogue or mimic thereof.

7. A pharmaceutical composition as claimed in claim 4, wherein said therapeutic agent is a nucleic acid.

8. A pharmaceutical composition as claimed in claim 4, wherein said therapeutic agent is calcitonin.

9. A pharmaceutical composition as claimed in claim 4, wherein said therapeutic agent is parathyroid hormone.

10. A pharmaceutical composition as claimed in claim 4, wherein said therapeutic agent is erythropoietin.

11. A pharmaceutical composition as claimed in claim 4, wherein said therapeutic agent is GM-CSF.

12. A pharmaceutical composition as claimed in claim 4, wherein said therapeutic agent is growth hormone.

13. A pharmaceutical composition as claimed in claim 4, wherein said therapeutic agent is a small molecule therapeutic.

14. A pharmaceutical composition as claimed in claim 4, wherein said composition is suitable for oral administration.

15. A method of opening the tight junctions of an epithelial surface comprising administering an effective amount of a peptide according to claim 1 to the epithelium.

16. A method of delivering an agent across an epithelial surface comprising administering said agent in conjunction with a peptide as claimed in claim 1.

17. A method as claimed in claim 15, wherein said method is carried out in vitro.

18. A method as claimed in claim 16, wherein said method is carried out in vitro.

19. A method of opening the tight junctions of an epithelial surface comprising administering an effective amount of a pharmaceutical composition according to claim 3 to the epithelium.

20. A method of delivering an agent across an epithelial surface comprising administering said agent in conjunction with a pharmaceutical composition as claimed in claim 3.

21. A method as claimed in claim 19, wherein said method is carried out in vitro.

22. A method as claimed in claim 20, wherein said method is carried out in vitro.

23. A method as claimed in claim 20, wherein the pharmaceutical composition comprises insulin, or a derivative, analogue or mimic thereof, or GLP-1, or a derivative, analogue or mimic thereof.

* * * * *

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: VARIANT
<222> LOCATION: (1)..(1)
<223> OTHER INFORMATION: Xaa1 any negatively charged amino acid residue,
    for example pTyr, Asp or Glu
<220> FEATURE:
<221> NAME/KEY: VARIANT
<222> LOCATION: (2)..(2)
<223> OTHER INFORMATION: Xaa2 is any small hydrophobic amino acid
    residue, for example Val or Ala
<220> FEATURE:
<221> NAME/KEY: VARIANT
<222> LOCATION: (3)..(3)
<223> OTHER INFORMATION: Xaa3 is any positively charged amino acid residue, for example Lys or Arg
<220> FEATURE:
<221> NAME/KEY: VARIANT
<222> LOCATION: (4)..(4)
<223> OTHER INFORMATION: Xaa4 is any hydrophillic amino acid residue,
      for exampleTyr, Phe, Thr or Ser
<220> FEATURE:
<221> NAME/KEY: VARIANT
<222> LOCATION: (5)..(5)
<223> OTHER INFORMATION: Xaa4 is anynegatively charged amino acid
      residue, for example PTyr, Asp or Glu

<400> SEQUENCE: 1

Tyr Val Lys Tyr Tyr
1               5

<210> SEQ ID NO 2
<211> LENGTH: 4
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
<222> LOCATION: (1)..(1)
<223> OTHER INFORMATION: Xaa at position 1 is any amino acid residue

<400> SEQUENCE: 2

Xaa Tyr Gln Tyr
1

<210> SEQ ID NO 3
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 3

Arg Arg Val Glu Val Lys Tyr Asp Arg Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 4

Arg Lys Ala Lys Tyr Gln Tyr Arg Arg Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
<222> LOCATION: (1)..(1)
<223> OTHER INFORMATION: Xaa is up to 10 positively charged amino acid
      residues
<220> FEATURE:
<221> NAME/KEY: VARIANT
<222> LOCATION: (2)..(2)
<223> OTHER INFORMATION: Xaa2 is a positively charged amino acid
      residues
<220> FEATURE:
<221> NAME/KEY: VARIANT

```
<222> LOCATION: (3)..(3)
<223> OTHER INFORMATION: Xaa3 is absent or a hydrophobic amino acid
      residues
<220> FEATURE:
<221> NAME/KEY: VARIANT
<222> LOCATION: (4)..(4)
<223> OTHER INFORMATION: Xaa4 is a negatively charged amino acid
      residues
<220> FEATURE:
<221> NAME/KEY: VARIANT
<222> LOCATION: (5)..(5)
<223> OTHER INFORMATION: Xaa5 is a small hydrophobic amino acid residues
<220> FEATURE:
<221> NAME/KEY: VARIANT
<222> LOCATION: (6)..(6)
<223> OTHER INFORMATION: Xaa6 is a positively charged amino acid
      residues
<220> FEATURE:
<221> NAME/KEY: VARIANT
<222> LOCATION: (7)..(7)
<223> OTHER INFORMATION: Xaa7 is a hydrophobic amino acid residues
<220> FEATURE:
<221> NAME/KEY: VARIANT
<222> LOCATION: (8)..(8)
<223> OTHER INFORMATION: Xaa8 is a negatively charged amino acid
      residues
<220> FEATURE:
<221> NAME/KEY: VARIANT
<222> LOCATION: (8)..(8)
<223> OTHER INFORMATION: Xaa8 is a negatively charged amino acid
      residues
<220> FEATURE:
<221> NAME/KEY: VARIANT
<222> LOCATION: (9)..(9)
<223> OTHER INFORMATION: Xaa9 is a positively charged amino acid
      residues
<220> FEATURE:
<221> NAME/KEY: VARIANT
<222> LOCATION: (10)..(10)
<223> OTHER INFORMATION: Xaa10 is up to 10 positively charged amino
      acid residues

<400> SEQUENCE: 5

Lys Lys Ala Asp Ala Lys Ala Asp Lys Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
<222> LOCATION: (1)..(1)
<223> OTHER INFORMATION: Xaa1 is absent or a hydrophobic amino acid
      residue
<220> FEATURE:
<221> NAME/KEY: VARIANT
<222> LOCATION: (2)..(2)
<223> OTHER INFORMATION: Xaa2 is a negatively charged amino acid residue
<220> FEATURE:
<221> NAME/KEY: VARIANT
<222> LOCATION: (3)..(3)
<223> OTHER INFORMATION: Xaa3 is a small hydrophobic amino acid residue
<220> FEATURE:
<221> NAME/KEY: VARIANT
<222> LOCATION: (4)..(4)
<223> OTHER INFORMATION: Xaa4 is a positively charged amino acid residue
<220> FEATURE:
<221> NAME/KEY: VARIANT
<222> LOCATION: (5)..(5)
<223> OTHER INFORMATION: Xaa5 is a hydrophobic amino acid residue
<220> FEATURE:
<221> NAME/KEY: VARIANT
<222> LOCATION: (6)..(6)
<223> OTHER INFORMATION: Xaa6 is a negatively charged amino acid residue
```

```
<220> FEATURE:
<221> NAME/KEY: VARIANT
<222> LOCATION: (7)..(7)
<223> OTHER INFORMATION: Xaa7 is a positively charged amino acid residue

<400> SEQUENCE: 6

Ala Asp Ala Lys Ala Asp Lys Lys
1               5

<210> SEQ ID NO 7
<211> LENGTH: 8
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
<222> LOCATION: (1)..(1)
<223> OTHER INFORMATION: Xaa1 is up to 10 positively charged amino acid
      residues
<220> FEATURE:
<221> NAME/KEY: VARIANT
<222> LOCATION: (2)..(2)
<223> OTHER INFORMATION: Xaa2 is a positively charged amino acid residue
<220> FEATURE:
<221> NAME/KEY: VARIANT
<222> LOCATION: (3)..(3)
<223> OTHER INFORMATION: Xaa3 is absent or a hydrophobic amino acid
      residue
<220> FEATURE:
<221> NAME/KEY: VARIANT
<222> LOCATION: (4)..(4)
<223> OTHER INFORMATION: Xaa4 is a negatively charged amino acid residue
<220> FEATURE:
<221> NAME/KEY: VARIANT
<222> LOCATION: (5)..(5)
<223> OTHER INFORMATION: Xaa5 is a small hydrophobic amino acid residue
<220> FEATURE:
<221> NAME/KEY: VARIANT
<222> LOCATION: (6)..(6)
<223> OTHER INFORMATION: Xaa6 is a positively charged amino acid residue
<220> FEATURE:
<221> NAME/KEY: VARIANT
<222> LOCATION: (7)..(7)
<223> OTHER INFORMATION: Xaa7 is a hydrophobic amino acid residue
<220> FEATURE:
<221> NAME/KEY: VARIANT
<222> LOCATION: (8)..(8)
<223> OTHER INFORMATION: Xaa8 is a negatively charged amino acid residue

<400> SEQUENCE: 7

Lys Lys Ala Asp Ala Lys Ala Asp
1               5

<210> SEQ ID NO 8
<211> LENGTH: 9
<212> TYPE: PRT
<213> ORGANISM: Artificial Sequence
<220> FEATURE:
<223> OTHER INFORMATION: drug delivery enhancement peptide

<400> SEQUENCE: 8

Arg Val Thr Val Lys Tyr Asp Arg Arg
1               5

<210> SEQ ID NO 9
<211> LENGTH: 12
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
```

```
<222> LOCATION: (1)..(1)
<223> OTHER INFORMATION: Xaa1 is up to 10 positively charged amino acid
      residues
<220> FEATURE:
<221> NAME/KEY: VARIANT
<222> LOCATION: (2)..(2)
<223> OTHER INFORMATION: Xaa2 is a positively charged amino acid
      residues
<220> FEATURE:
<221> NAME/KEY: VARIANT
<222> LOCATION: (3)..(3)
<223> OTHER INFORMATION: Xaa3 is a Ala or Val
<220> FEATURE:
<221> NAME/KEY: VARIANT
<222> LOCATION: (4)..(4)
<223> OTHER INFORMATION: Xaa4 is absent or Ala or 1, 2, 3 or 4
      positively charged amino acid residues
<220> FEATURE:
<221> NAME/KEY: VARIANT
<222> LOCATION: (6)..(6)
<223> OTHER INFORMATION: Xaa6 is a positively charged amino acid residue
<220> FEATURE:
<221> NAME/KEY: VARIANT
<222> LOCATION: (6)..(6)
<223> OTHER INFORMATION: Xaa6 is a positively charged amino acid residue
<220> FEATURE:
<221> NAME/KEY: VARIANT
<222> LOCATION: (9)..(9)
<223> OTHER INFORMATION: Xaa9 is absent or Ala or 1, 2, 3 or 4
      positively charged amino acid residue
<220> FEATURE:
<221> NAME/KEY: VARIANT
<222> LOCATION: (10)..(10)
<223> OTHER INFORMATION: Xaa10 is a positively charged amino acid
      residue
<220> FEATURE:
<221> NAME/KEY: VARIANT
<222> LOCATION: (12)..(12)
<223> OTHER INFORMATION: Xaa12 is up to 10  positively charged amino
      acid residues

<400> SEQUENCE: 9

Lys Lys Ala Ala Lys Tyr Gln Tyr Ala Lys Lys Lys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
<222> LOCATION: (1)..(1)
<223> OTHER INFORMATION: Xaa1 is up to 10 positively charged amino acid
      residues
<220> FEATURE:
<221> NAME/KEY: VARIANT
<222> LOCATION: (2)..(2)
<223> OTHER INFORMATION: Xaa2 is a positively charged amino acid residue
<220> FEATURE:
<221> NAME/KEY: VARIANT
<222> LOCATION: (3)..(3)
<223> OTHER INFORMATION: Xaa3 is Ala or Val
<220> FEATURE:
<221> NAME/KEY: VARIANT
<222> LOCATION: (4)..(4)
<223> OTHER INFORMATION: Xaa4 is absent or Ala or 1, 2, 3, or 4
      positively charged amino acid resdiues
<220> FEATURE:
<221> NAME/KEY: VARIANT
<222> LOCATION: (5)..(5)
<223> OTHER INFORMATION: Xaa5 is a positively charged amino acid resdiue
<220> FEATURE:
<221> NAME/KEY: VARIANT
<222> LOCATION: (5)..(5)
<223> OTHER INFORMATION: Xaa5 is a positively charged amino acid resdiue
```

```
<220> FEATURE:
<221> NAME/KEY: VARIANT
<222> LOCATION: (9)..(9)
<223> OTHER INFORMATION: Xaa9 is absent or Ala or 1, 2, 3, or 4
      positively charged amino acid resdiues

<400> SEQUENCE: 10

Lys Lys Ala Ala Lys Tyr Gln Tyr Ala
1               5

<210> SEQ ID NO 11
<211> LENGTH: 10
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: VARIANT
<222> LOCATION: (1)..(1)
<223> OTHER INFORMATION: Xaa1 is Ala or Val
<220> FEATURE:
<221> NAME/KEY: VARIANT
<222> LOCATION: (1)..(1)
<223> OTHER INFORMATION: Xaa1 is Ala or Val
<220> FEATURE:
<221> NAME/KEY: VARIANT
<222> LOCATION: (2)..(2)
<223> OTHER INFORMATION: Xaa2 is absent or Ala or 1, 2, 3 or 4
      positively charged amino acid residues
<220> FEATURE:
<221> NAME/KEY: VARIANT
<222> LOCATION: (3)..(3)
<223> OTHER INFORMATION: Xaa3 is a  positively charged amino acid
      residue
<220> FEATURE:
<221> NAME/KEY: VARIANT
<222> LOCATION: (7)..(7)
<223> OTHER INFORMATION: Xaa7 is absent or Ala, or 1, 2 3, or 4
      positively charged amino acid residues
<220> FEATURE:
<221> NAME/KEY: VARIANT
<222> LOCATION: (8)..(8)
<223> OTHER INFORMATION: Xaa8 is a positively charged amino acid residue
<220> FEATURE:
<221> NAME/KEY: VARIANT
<222> LOCATION: (8)..(8)
<223> OTHER INFORMATION: Xaa8 is a positively charged amino acid residue
<220> FEATURE:
<221> NAME/KEY: VARIANT
<222> LOCATION: (10)..(10)
<223> OTHER INFORMATION: Xaa10 is up to 10 positively charged amino acid
      residues

<400> SEQUENCE: 11

Ala Ala Lys Tyr Gln Tyr Ala Lys Lys Lys
1               5                   10

<210> SEQ ID NO 12

<400> SEQUENCE: 12

000

<210> SEQ ID NO 13
<211> LENGTH: 9
<212> TYPE: PRT
<213> ORGANISM: Artificial Sequence
<220> FEATURE:
<223> OTHER INFORMATION: drug delivery enhancement peptide

<400> SEQUENCE: 13

Arg Val Thr Val Lys Tyr Asp Arg Arg
1               5
```

<210> SEQ ID NO 14
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 14

Arg Arg Val Thr Val Lys Tyr Asp Arg Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: MOD_RES
<222> LOCATION: (4)..(4)
<223> OTHER INFORMATION: PHOSPHORYLATION

<400> SEQUENCE: 15

Arg Arg Val Thr Val Lys Tyr Asp Arg Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 16

Arg Arg Val Thr Val Lys Tyr Lys Arg Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: drug delivery enhancement peptide
<220> FEATURE:
<221> NAME/KEY: MOD_RES
<222> LOCATION: (4)..(4)
<223> OTHER INFORMATION: PHOSPHORYLATION

<400> SEQUENCE: 17

Arg Arg Val Thr Val Lys Tyr Lys Arg Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 18

Arg Arg Lys Thr Val Lys Tyr Asp Arg Arg
1               5                   10

<210> SEQ ID NO 19
<211> LENGTH: 6
<212> TYPE: PRT
<213> ORGANISM: Artificial Sequence

```
<220> FEATURE:
<223> OTHER INFORMATION: drug delivert enhancement peptide

<400> SEQUENCE: 19

Lys Ala Lys Tyr Gln Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 20

Arg Arg Asp Tyr Lys Val Glu Val Arg Arg
1               5                   10

<210> SEQ ID NO 21
<211> LENGTH: 10
<212> TYPE: PRT
<213> ORGANISM: Artificial Sequence
<220> FEATURE:
<223> OTHER INFORMATION: drug delivery enhancement peptide

<400> SEQUENCE: 21

Lys Arg Arg Tyr Gln Tyr Lys Ala Lys Arg
1               5                   10
```